United States Patent
Janssens et al.

(12) 
(10) Patent No.: US 6,521,621 B1
(45) Date of Patent: *Feb. 18, 2003

(54) 1-(1,2-DISUBSTITUTED PIPERIDINYL)-4-SUBSTITUTED PIPERAZINE DERIVATIVES

(75) Inventors: Frans Eduard Janssens, Bonheiden (BE); François Maria Sommen, Wortel (BE); Dominique Louis Nestor Ghislaine Surleraux, Machelen (BE); Joseph Elisabeth Leenaerts, Rijkevorsel (BE); Yves Emiel Maria Van Roosbroeck, Heist-op den-Berg (BE)

(73) Assignee: Janssen Pharmaceutica N.V. (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/745,513

(22) Filed: Dec. 22, 2000

Related U.S. Application Data

(63) Continuation of application No. 09/054,963, filed on Apr. 3, 1998, now Pat. No. 6,197,722, which is a continuation of application No. PCT/EP96/04660, filed on Oct. 25, 1996.

(30) Foreign Application Priority Data

Oct. 30, 1995 (EP) .............................................. 95202929

(51) Int. Cl.[7] .................... A61K 31/496; A61K 31/497; A61K 31/498; C07D 401/14; C07D 413/14
(52) U.S. Cl. .................. 514/248; 514/249; 514/252.11; 514/252.18; 514/252.02; 514/253.01; 514/253.09; 514/253.1; 514/253.13; 514/253.06; 544/236; 544/238; 544/295; 544/357; 544/353; 544/355; 544/360; 544/362; 544/363; 544/364; 544/365
(58) Field of Search ................................. 544/360, 362, 544/363, 364, 365, 238, 295, 353, 355, 357, 236; 514/253.01, 253.09, 253.1, 253.13, 253.06, 249, 248, 252.11, 252.18, 252.02

(56) References Cited

U.S. PATENT DOCUMENTS

| | | | |
|---|---|---|---|
| 5,310,743 A | 5/1994 | Schilling et al. | 514/311 |
| 5,340,822 A | 8/1994 | Edmonds-Alt et al. | 514/316 |
| 5,814,636 A | 9/1998 | Katano et al. | 514/252 |
| 5,935,951 A | 8/1999 | Ofner et al. | 514/227.8 |
| 6,197,772 B1 * | 3/2001 | Janssens et al. | |

FOREIGN PATENT DOCUMENTS

| | | |
|---|---|---|
| EP | 0 512 901 | 11/1992 |
| EP | 0 532 456 | 3/1993 |
| EP | 0 625 509 | 11/1994 |
| EP | 0 655 442 | 5/1995 |
| WO | WO 95/11895 | 10/1993 |
| WO | WO 96/10562 | 4/1996 |

OTHER PUBLICATIONS

Rouissi et al, *Biochemical & Biophysical Research Communications 176*, p. 894–901, 1991.*
Maggi et al, *J. Auton. Pharmacol.* 13 p. 23–93, 1993.*
Ohmact et al in *Annual Reports in Medicinal Chemistry*, vol. 33, p. 71–80, 1998.*

* cited by examiner

*Primary Examiner*—Emily Bernhardt
(74) *Attorney, Agent, or Firm*—Mary Appollina

(57) ABSTRACT

This invention concerns the compounds of formula (I)

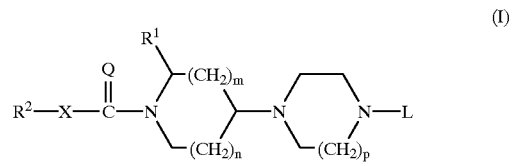

the N-oxide forms, the pharmaceutically acceptable addition salts and the stereoisomeric forms thereof, wherein n is 0, 1 or 2; m is 1 or 2, provided that if m is 2, then n is 1; p is 1 or 2; =Q is =O or =NR$^3$; X is a covalent bond or a bivalent radical of formula —O—, —S—, —NR$^3$—; R$^1$ is Ar$^1$, Ar$^1$C$_{1-6}$alkyl or di(Ar$^1$)C$_{1-6}$alkyl, wherein each C$_{1-6}$alkyl group is optionally substituted with hydroxy, C$_{1-4}$alkyloxy, oxo or a ketalized oxo substituent; R$^2$ is Ar$^2$, Ar$^2$C$_{1-6}$alkyl, Het$^1$ or Het$^1$C$_{1-6}$alkyl; R$^3$ is hydrogen or C$_{1-6}$alkyl; L is hydrogen; Ar$^3$; C$_{1-6}$alkyl; C$_{1-6}$alkyl substituted with 1 or 2 substituents selected from hydroxy, C$_{1-6}$alkyloxy, Ar$^3$, Ar$^3$C$_{1-6}$alkyloxy and Het$^2$; C$_{3-6}$alkenyl; Ar$^3$C$_{3-6}$alkenyl; di(Ar$^3$)C$_{3-6}$alkenyl or a radical of formula (a-1), (a-2), (a-3), (a-4) or (a-5); Ar$^1$, Ar$^2$ and Ar$^3$ are each phenyl or substituted phenyl; Het$^1$ and Het$^2$ are each monocyclic or a bicyclic heterocycles; as substance-P antagonists; their preparation, compositions containing them and their use as a medicine.

10 Claims, No Drawings

1-(1,2-DISUBSTITUTED PIPERIDINYL)-4-SUBSTITUTED PIPERAZINE DERIVATIVES

This application is a continuing application of Ser. No. 09/054,963, filed Apr. 3, 1998 and now U.S. Pat. No. 6,197,772 B1 which issued on Mar. 6, 2001 which is a continuation of PCT/EP96/04660 filed Oct. 25, 1996.

This invention concerns 1-(1,2-disubstituted piperidinyl)-4-substituted piperazine derivatives having tachykinin antagonistic activity, in particular substance P antagonistic activity, and their preparation; it further relates to compositions comprising them, as well as their use as a medicine.

Substance P is a naturally occurring neuropeptide of the tachykinin family. There are ample studies showing that substance P and other tachykinins are involved in a variety of biological actions, and therefore, play an essential role in various disorders (Regoli et al., Pharmacological Reviews 46(4), 1994, p. 551–599, "Receptors and Antagonists for Substance P and Related Peptides"). The development of tachykinin antagonists has led to date to a series of peptide compounds of which might be anticipated that they are metabolically too labile to be employed as pharmaceutically active substances (Longmore J. et al., DN&P 8(1), February 1995, p. 5–23, "Neurokinin Receptors"). The present invention concerns nonpeptide tachykinin antagonists, in particular nonpeptide substance-P antagonists, which in general are metabolically more stable, and hence, may be more appropriate as pharmaceutically active substances.

Several nonpeptide tachykinin antagonists are disclosed in the art. For instance, EP-0,532,456-A, published on Mar. 17, 1993 by Ciba-Geigy Corp., discloses 1-acylpiperidine compounds, in particular 2-arylalkyl-1-arylcarbonyl-4-piperidinamine derivatives, and their use as substances antagonists. EP-0,655,442-A, published on May 31, 1995 by Fujisawa Pharmaceutical Co. Ltd., discloses piperazine derivatives having tachykinin antagonistic activity.

The present compounds differ therefrom in that they invariably contain a 4-substituted-(piperazine or homopiperazine)-moiety in the 4-position of a piperidine- or homopiperidine group or in the 3-position of a pyrrolidine group, and by their favourable farmacological properties.

The present invention concerns compounds of formula

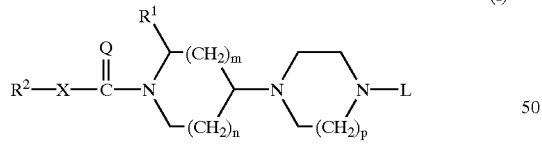

(I)

the N-oxide forms, the pharmaceutically acceptable addition salts and the stereochemically isomeric forms thereof, wherein n is 0, 1 or 2;
m is 1 or 2, provided that if m is 2, then n is 1;
p is 1 or 2;
=Q is =O or =NR$^3$;
X is a covalent bond or a bivalent radical of formula —O—, —S—, —NR$^3$—;
R$^1$ is Ar$^1$, Ar$^1$C$_{1-6}$alkyl or di(Ar$^1$)C$_{1-6}$alkyl, wherein each C$_{1-6}$alkyl group is optionally substituted with hydroxy, C$_{1-4}$alkyloxy, oxo or a ketalized oxo substituent of formula —O—CH$_2$—CH$_2$—O— or —O—CH$_2$—H$_2$—H$_2$—O—;
R$^2$ is Ar$^2$, Ar$^2$C$_{1-6}$alkyl, Het$^1$ or Het$^1$C$_{1-6}$alkyl;
R$^3$ is hydrogen or C$_{1-6}$alkyl;
L is hydrogen; Ar$^3$; C$_{1-6}$alkyl; C$_{1-6}$alkyl substituted with 1 or 2 substituents selected from hydroxy, C$_{1-6}$alkyloxy, Ar$^3$, Ar$^3$C$_{1-6}$alkyloxy and Het$^2$; C$_{3-6}$alkenyl; Ar$^3$C$_{3-6}$alkenyl; di(Ar$^3$)C$_{3-6}$alkenyl or a radical of formula

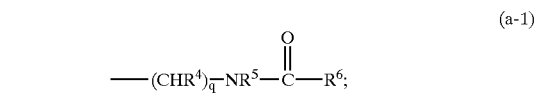

(a-1)

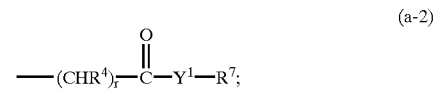

(a-2)

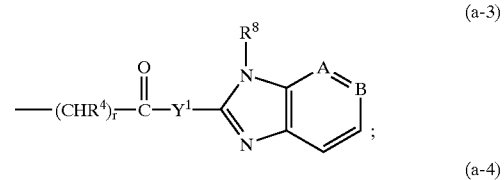

(a-3)

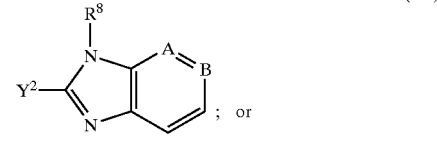

; or (a-4)

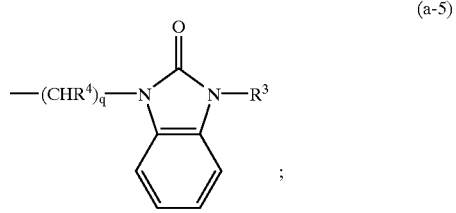

; (a-5)

wherein each q independently is 2, 3 or 4;
each r is 1, 1, 2, 3 or 4;
each Y$^1$ independently is a covalent bond, —O— or NR$^3$;
Y$^2$ is a covalent bond, C$_{1-4}$alkanediyl or —C$_{1-4}$alkylNR$^3$—;
each —A=B— independently is a bivalent radical of formula —CH=CH—, —N=CH— or —CH=N—;
each R$^4$ independently is hydrogen, C$_{1-6}$alkyl, Ar$^2$ or Ar$^2$C$_{1-6}$alkyl;
R$^5$ is hydrogen, C$_{1-6}$alkyl or Ar$^3$;
R$^6$ is C$_{1-6}$alkyl, Ar$^3$, Ar$^3$C$_{1-6}$alkyl, di(Ar$^3$)C$_{1-6}$alkyl, Ar$^3$C$_{3-7}$cycloalkyl, or indolyl;
R$^7$ is Ar$^3$; Ar$^3$C$_{1-6}$alkyl; di(Ar$^3$)C$_{1-6}$alkyl; C$_{1-6}$alkyl; C$_{3-7}$cycloalkyl; C$_{3-7}$cycloalkyl substituted with Ar$^3$; oxazolyl; oxazolyl substituted with halo or C$_{1-6}$alkyl; thiazolyl; thiazolyl substituted with halo or C$_{1-6}$alkyl; imidazolyl; imidazolyl substituted with Ar$^3$, C$_{1-6}$alkyl, Ar$^3$C$_{1-6}$alkyl or halo; indolinyl; indolinyl substituted with C$_{1-4}$alkyl; 2,3,4-trihydroquinolinyl; pyrrolidinyl or furanyl;
each R$^8$ independently is hydrogen, C$_{1-6}$alkyl, C$_{3-7}$cycloalkyl or a radical of formula —Alk—R$^{11}$ (b-1) or
—Alk—Z—R$^{12}$ (b-2);

wherein Alk is C$_{1-6}$alkanediyl;
Z is a bivalent radical of formula —O—, —S— or —NR$^3$—;

$R^{11}$ is phenyl; phenyl substituted with 1 or 2 substituents selected from halo, $C_{1-6}$alkyl or $C_{1-6}$alkyloxy; furanyl; furanyl substituted with 1 or 2 substituents selected from $C_{1-6}$alkyl or hydroxy$C_{1-6}$alkyl; thienyl; thienyl substituted with 1 or 2 substituents selected from halo or $C_{1-6}$alkyl; oxazolyl; oxazolyl substituted with 1 or 2 $C_{1-6}$alkyl substituents; thiazolyl; thiazolyl substituted with 1 or 2 $C_{1-6}$alkyl substituents; pyridinyl or pyridinyl substituted with 1 or 2 $C_{1-6}$alkyl substituents;

$R^{12}$ is $C_{1-6}$alkyl or $C_{1-6}$alkyl substituted with hydroxy, carboxyl or $C_{1-6}$alkyloxycarbonyl;

$Ar^1$ is phenyl; phenyl substituted with 1, 2 or 3 substituents each independently selected from halo, $C_{1-4}$alkyl, halo$C_{1-4}$alkyl, cyano, aminocarbonyl, $C_{1-4}$alkyloxy or halo$C_{1-4}$alkyloxy;

$Ar^2$ is naphtalenyl; phenyl; phenyl substituted with 1, 2 or 3 substituents each independently selected from hydroxy, halo, cyano, nitro, amino, mono- or di($C_{1-4}$alkyl)amino, $C_{1-4}$alkyl, halo$C_{1-4}$alkyl, $C_{1-4}$alkyloxy, halo$C_{1-4}$alkyloxy, carboxyl, $C_{1-4}$alkyloxycarbonyl, aminocarbonyl and mono- or di($C_{1-4}$alkyl) aminocarbonyl;

$Ar^3$ is phenyl or phenyl substituted with 1, 2 or 3 substituents selected from halo, hydroxy, amino, nitro, aminocarbonyl, $C_{1-6}$alkyl, halo$C_{1-6}$alkyl or $C_{1-6}$alkyl-oxy;

$Het^1$ is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl or mono-, di- or tri(halo)methyl; and $Het^2$ is a heterocycle selected from 1,4-dihydro-5-oxo-tetrazol-1-yl, imidazo[1,2-a]-pyridinyl, oxazolyl or imidazolyl; each of said heterocycles may be substituted with 1 or where possible 2 substituents selected from $C_{1-4}$alkyl and $Ar^3$.

The heterocycles in the definition of $Het^1$ are preferably connected to the rest of the molecule, i.e. X, —C(=Q)— or $C_{1-6}$alkyl, by a carbon atom.

As used in the foregoing definitions and hereinafter, halo is generic to fluoro, chloro, bromo and iodo; $C_{2-4}$alkyl defines straight and branched chain saturated hydrocarbon radicals having from 2 to 4 carbon atoms such as, for example, ethyl, propyl, butyl, 1-methylethyl, 2-methylpropyl and the like; $C_{1-4}$alkyl is meant to include $C_{2-4}$alkyl and methyl; $C_{1-5}$alkyl is meant to include $C_{1-4}$alkyl and the higher homologues thereof having 5 carbon atoms such as, for example, pentyl, 2-methylbutyl and the like; $C_{1-6}$alkyl is meant to include $C_{1-5}$alkyl and the higher homologues thereof having 6 carbon atoms such as, for example, hexyl, 2-methylpentyl and the like; $C_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl, and the like; $C_{1-6}$alkanediyl is meant to include $C_{1-4}$alkanediyl and the higher homologues thereof having form 5 to 6 carbon atoms such as, for example, 1,5-pentanediyl, 1,6-hexanediyl and the like; $C_{3-6}$alkenyl defines straight and branched chain hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl, 3-hexenyl and the like; and the carbon of said $C_{3-6}$alkenyl connected to the nitrogen atom of the piperazine or homopiperazine preferably is saturated.

As used in the foregoing definitions and hereinafter, halo$C_{1-4}$alkyl is defined as mono- or polyhalosubstituted $C_{1-4}$alkyl, in particular $C_{1-4}$alkyl substituted with 1 to 6 halogen atoms, more in particular difluoro- or trifluoromethyl.

The pharmaceutically acceptable addition salts as mentioned hereinabove are meant to comprise the therapeutically active non-toxic acid addition salt forms which the compounds of formula (I) are able to form. Said salts can conveniently be obtained by treating the base form of the compounds of formula (I) with appropriate acids such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, famaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

For isolation and purification purposes, it is also possible to use pharmaceutically unacceptable salts. Only the pharmaceutically acceptable, non-toxic salts are used therapeutically and those salts are therefore preferred.

The term "stereochemically isomeric forms" as used hereinbefore defines all the possible isomeric as well as conformational forms which the compounds of formula (I) may possess. Unless otherwise mentioned or indicated, the chemical designation of compounds denotes the mixture, more in particular the racemic mixture, of all possible stereochemically and conformationally isomeric forms, said mixtures containing all diastereomers, enantiomers and/or conformers of the basic molecular structure. More in particular, stereogenic centers may have the R- or S-configuration; substituents on bivalent cyclic saturated radicals may have either the cis- or trans-configuration; >C=NR$^3$ and $C_{3-6}$alkenyl radicals may have the E- or Z-configuration. The compounds of formula (I) have at least two stereogenic centers; thus for compounds of which the actual stereochemical configuration is known, the relative stereodescriptors R* and S* may be used in accordance with the Chemical Abstracts rules (Chemical Substance Name Selection Manual (CA), 1982 Edition, Vol. III, Chapter 20). In those cases where the compounds of formula (I) were separated into its racemic cis and racemic trans isomers, or in those cases where the racemic cis or racemic trans isomers were separated into its pure enantiomeric forms, the stereochemically isomeric form which was first isolated was designated as "A" and the second as "B". All stereochemically isomeric forms of the compounds of formula (I) both in pure form or mixtures thereof are intended to be embraced within the scope of the present invention.

Some of the compounds of formula (I) may also exist in their tautomeric form. Such forms although not explicitly indicated in the above formula are intended to be included within the scope of the present invention. For instance, compounds of formula (I) wherein L is a radical of formula (a-1) wherein $R^5$ is hydrogen, or a radical of (a-2) or (a-3) wherein $Y^1$ is —NH—, or a radical of formula (a-5) wherein $R^3$ is hydrogen may exist in their corresponding tautomeric form. Also compounds of formula (I) wherein X is —NH— and =Q is =O may exist in their corresponding tautomeric form.

The N-oxide forms of the compounds of formula (I) are meant to comprise those compounds of formula (I) wherein one or several nitrogen atoms are oxidized to the so-called N-oxide, particularly those N-oxides wherein one or more of the piperazine-nitrogens are N-oxidized.

Whenever used hereinafter, the term "compounds of formula (I)" is meant to also include their N-oxide forms, their pharmaceutically acceptable addition salts, and their stereochemically isomeric forms.

A special group of compounds are those compounds of formula (I) wherein L is hydrogen; $C_{1-6}$alkyl; $C_{1-6}$alkyl substituted with hydroxy; $C_{3-6}$alkenyl; $Ar^3$; $Ar^3C_{1-6}$alkyl; di($Ar^3$)$C_{1-6}$alkyl; $Ar^3C_{3-6}$alkenyl; di($Ar^3$)$C_{1-6}$alkenyl; or a radical of formula (a-1), (a-2), (a-4) or (a-5) wherein $R^7$ is $Ar^3$; $Ar^3C_{1-6}$alkyl; di($Ar^3$)$C_{1-6}$alkyl; $C_{1-6}$alkyl; $C_{3-7}$cycloalkyl; $C_{3-7}$cycloalkyl substituted with $Ar^3$; oxazolyl; oxazolyl substituted with halo or $C_{1-6}$alkyl; thiazolyl; thiazolyl substituted with halo or $C_{1-6}$alkyl; imidazolyl; imidazolyl substituted with $Ar^3$, $C_{1-6}$alkyl, $Ar^3C_{1-6}$alkyl or halo; pyrrolidinyl or furanyl;

$Ar^3$ is phenyl or phenyl substituted with 1, 2 or 3 substituents selected from halo, hydroxy, amino, aminocarbonyl, $C_{1-6}$alkyl, halo$C_{1-6}$alkyl or $C_{1-6}$alkyloxy;

$Het^1$ is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl or mono-, di- or tri(halo)methyl.

A first group of interesting compounds consists of those compounds of formula (I) wherein one or more of the following restrictions apply:

a) $R^1$ is $Ar^1C_{1-6}$alkyl; or b) $R^2$ is $Ar^2$, $Ar^2C_{1-6}$alkyl or $Het^1$; in particular, phenyl substituted with 1, 2 or 3 substituents each independently selected from halo, cyano, nitro, amino, $C_{1-4}$alkyl, halo$C_{1-4}$alkyl, $C_{1-4}$alkyloxy and $C_{1-4}$alkyloxycarbonyl, more in particular, phenyl substituted with 2 substituents selected from methyl and trifluoromethyl; or c) n is 0 or 1, in particular n is 1; or d) m is 1; or e) p is 1 or 2, in particular p is 1; or f) =Q is =O; or g) X is a covalent bond, —O— or —$NR^3$—, in particular a covalent bond.

A second group of interesting compounds consists of those compounds of formula (I) wherein L is hydrogen, $Ar^3$; $Ar^3C_{1-6}$alkyl; di($Ar^3$)$C_{1-6}$alkyl; $Ar^3C_{3-6}$alkenyl; $C_{1-6}$alkyl substituted with hydroxy; or a radical of formula (a-2) wherein
  $R^4$ is hydrogen or $Ar^2$;
  r is 0 or 1;
  $Y^1$ is a covalent bond, —O— or —$NR^3$—; and
  $R^7$ is $Ar^3$, $C_{3-7}$cycloalkyl substituted with $Ar^3$, di($Ar^3$) methyl, pyrrolidinyl or furanyl; or a radical of formula (a-4) wherein
  $Y^2$ a covalent bond or methylene;
  —A=B— is —CH=CH— or —N=CH—; and
  $R^8$ hydrogen, a radical of formula (b-1) wherein $R^{11}$ is methyl substituted oxazolyl, or a radical of formula (b-2) wherein Z is —O— and $R^{12}$ is $C_{1-6}$alkyl; or a radical of formula (a-5) wherein
  $R^4$ is hydrogen;
  q 2; and
  $R^3$ is hydrogen.

A third group of interesting compounds consists of those compounds of formula (I) wherein
  q is 2 or 4;
  —A=B— is —CH=CH— or —N=CH—;
  $R^4$ is hydrogen or $Ar^2$;
  $R^5$ is hydrogen;
  $R^6$ is $C_{1-6}$alkyl or $Ar^3$;
  $R^7$ is $Ar^3$; di($Ar^3$)$C_{1-6}$alkyl; $C_{1-6}$alkyl; $C_{3-7}$cycloalkyl substituted with $Ar^3$; thiazolyl; imidazolyl substituted with $C_{1-6}$alkyl or $Ar^3C_{1-6}$alkyl; indolinyl; indolinyl substituted with $C_{1-4}$alkyl; 2,3,4-trihydroquinolinyl; pyrrolidinyl or furanyl;
  Z is —O—;
  $R^{11}$ is phenyl substituted with halo; oxazolyl substituted with $C_{1-6}$alkyl; or
  $R^{12}$ is $C_{1-6}$alkyl.

Of special interest are those compounds of formula (I) wherein $R^1$ is $Ar^1C_{1-6}$alkyl, $R^2$ is phenyl substituted with 2 substituents selected from methyl or trifluoromethyl, X is a covalent bond and =Q is =O.

Further of special interest are those compounds of formula (I) wherein n and m are 1 and p is 1 or 2.

Particular compounds are those compounds of formula (I) wherein
  $R^1$ is phenylmethyl;
  $R^2$ is phenyl substituted with 2 substituents selected from methyl or trifluoromethyl;
  n, m and p are 1;
  X is a covalent bond; and
  =Q is =O.

Also particular compounds are those compounds of formula (I) wherein L is a radical of formula (a-2) wherein
  $R^4$ is hydrogen or phenyl;
  r is 0 or 1;
  $Y^1$ is a covalent bond, —O— or —NH—;

R[7] is pyrrolidinyl; furanyl; 1-phenylcyclohexanyl; diphenylmethyl; or phenyl substituted with 1, 2 or 3 substituents each independently selected from methyl, methoxy or chloro.

Preferred compounds are those particular compounds that have a trans configuration.

Other preferred compounds are those particular compounds that have a cis configuration.

Still other preferred compounds are those compounds of formula (I) wherein
R[1] is phenylmethyl;
R[2] is phenyl substituted with 2 substituents selected from methyl or trifluoromethyl;
n, m and p are 1;
X is a covalent bond;
=Q is =O;
L is a radical of formula (a-2) wherein
  R[4] is hydrogen;
  r is 1;
  Y[1] is —NH—; and
  R[7] is phenyl substituted with 2 methyl substituents.

Most preferred are those compounds selected from
4-[1-[3,5-bis(trifluoromethyl)benzoyl]-2-(phenylmethyl)-4-piperidinyl]-N-(2,6-dimethylphenyl)-1-piperazine acetamide;
4-[1-[3,5-bis(trifluoromethyl)benzoyl]-2-(phenylmethyl)-4-piperidinyl]-N-(1-phenylcyclohexyl)-1-piperazine acetamide;
1-[3,5-bis(trifluoromethyl)benzoyl]-2-(phenylmethyl)-4-[4-[(α-(1-pyrrolidinylcarbonyl)-benzyl]-1-piperazinyl] piperidine;
1-[3,5-bis(trifluoromethyl)benzoyl]-4-[4-[1-[(2-methyl-5-oxazolyl)methyl]-1H-benzimidazol-2-yl]-1-piperazinyl]-2-(phenylmethyl)piperidine;
4-[1-[3,5-bis(trifluoromethyl)benzoyl]-2-[(4-trifluoromethylphenyl)methyl]-4-piperidinyl]-N-(2,6-dimethylphenyl)-1-piperazine acetamide;
4-[1-[3,5-bis(trifluoromethyl)benzoyl]-2-[(3,4-dichlorophenyl)methyl]-4-piperidinyl]-N-(2,6-dimethylphenyl)-1-piperazine acetamide; the N-oxides, the stereoisomeric forms
and the pharmaceutically acceptable addition salts thereof.

Particularly interesting stereoisomeric forms are
(+)-(B)-trans-4-[1-[3,5-bis(trifluoromethyl)benzoyl]-2-(phenylmethyl)-4-piperidinyl]-N-(2,6-dimethylphenyl)-1-piperazine acetamide; and
(−)-(B)-cis-4-[1-[3,5-bis(trifluoromethyl)-benzoyl]-2-(phenylmethyl)-4-piperidinyl]-N-(2,6-dimethylphenyl)-1-piperazine acetamide, and the pharmaceutically acceptable addition salts thereof, especially the (L)-malic acid form.

The compounds of formula (I) can be prepared by reductively N-alkylating an inter-mediate of formula (III) with an intermediate of formula (II). Said reductive N-alkylation may be performed in a reaction-inert solvent such as, for example, dichloromethane, ethanol, toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium(IV)isopropylate as described in J. Org. Chem, 1990, 55, 2552–2554. Using said complex-forming agent may also result in an improved cis/trans ratio in favour of the trans isomer. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

$$R^2-X-\overset{Q}{\underset{\|}{C}}-N\begin{array}{c}R^1\\ \diagup(CH_2)_m\\ \diagdown(CH_2)_n\end{array}=O \quad +$$

(II)

$$H-N\begin{array}{c}\diagup\\ \diagdown(CH_2)_p\end{array}N-L \quad \xrightarrow{\text{reductive N-alkylation}} \quad (I)$$

(III)

In this and the following preparations, the reaction products may be isolated from the reaction medium and, if necessary, further purified according to methodologies generally known in the art such as, for example, extraction, crystallization, trituration and chromatography.

The compounds of formula (I) can also be prepared by reacting an intermediate of formula (IV) wherein W[1] is an appropriate leaving group such as, for example, a halogen, e.g. chloro or bromo, or a sulfonyloxy leaving group, e.g. methanesulfonyloxy or benzenesulfonyloxy, with an intermediate of formula (V). The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried at a temperature ranging between room temperature and reflux temperature.

$$R^2-X-\overset{Q}{\underset{\|}{C}}-W^1 \quad +$$

(IV)

$$H-N\begin{array}{c}\diagup(CH_2)_m\\ R^1\\ \diagdown(CH_2)_n\end{array}N\begin{array}{c}\diagup\\ \diagdown(CH_2)_p\end{array}N-L \quad \xrightarrow{\text{base}} \quad (I)$$

(V)

The compounds of formula (I) may also be converted into each other following art-known transformations. In particular, the compounds of formula (I) wherein L is other than hydrogen, said L being represented by L' and said compounds being represented by formula (I-a), can also be prepared by reacting a compound of formula (I) wherein L is hydrogen, said compounds being represented by formula (I-b), with an intermediate of formula (VI) wherein $W^2$ is an appropriate leaving group such as, for example, a halogen, e.g. chloro or bromo, or a sulfonyloxy leaving group, e.g. methanesulfonyloxy or benzenesulfonyloxy, at reaction conditions which are similar to those for the reaction between intermediates of formula (IV) and (V).

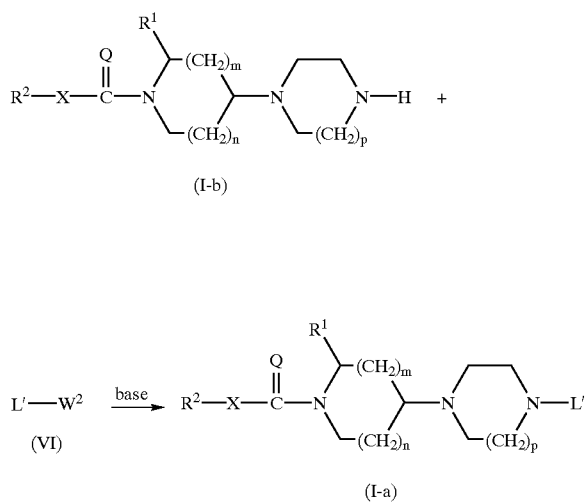

Compounds of formula (I-b) may be prepared by reductively N-alkylating a piperazine derivative of formula (VII) wherein $P^1$ is a protective group such as, for example, benzyl, with an intermediate of formula (II). Said reaction may be performed in a similar way as described hereinabove for the reductive N-alkylation using intermediates (II) and (III). The thus formed compound of formula (I-c) may then be deprotected using art-known deprotection techniques.

Depending on the nature of the protective group $P^1$, compounds of formula (I-c) may be part of the scope of the compounds of formula (I).

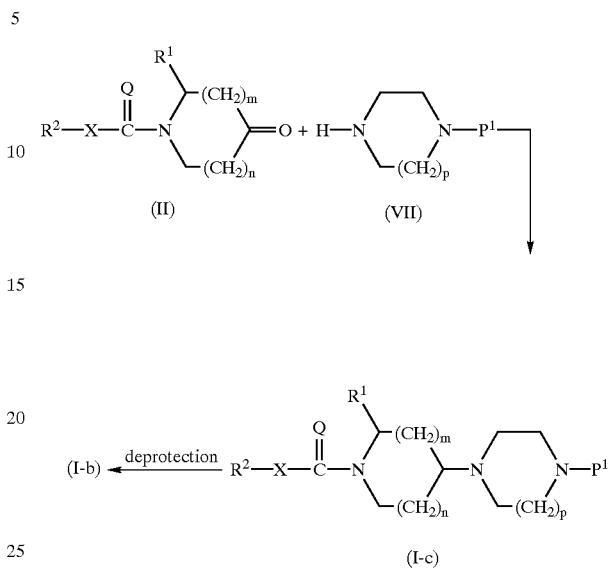

Alternatively, compounds of formula (I-b) may be prepared by first reductively N-alkylating a piperazine derivative of formula (VII) wherein $P^1$ is a protective group such as, for example, halo, with an intermediate of formula (VIII) using the same procedure as described hereinabove for the reductive N-alkylation using intermediates (II) and (III). The thus formed intermediate of formula (XI) may then be reacted with an intermediate of formula (IV) in a reaction-inert solvent and optionally in the presence of a suitable base such as, for example, triethylamine, to form a compound of formula (I-c), which may then be deprotected using art-known deprotection techniques.

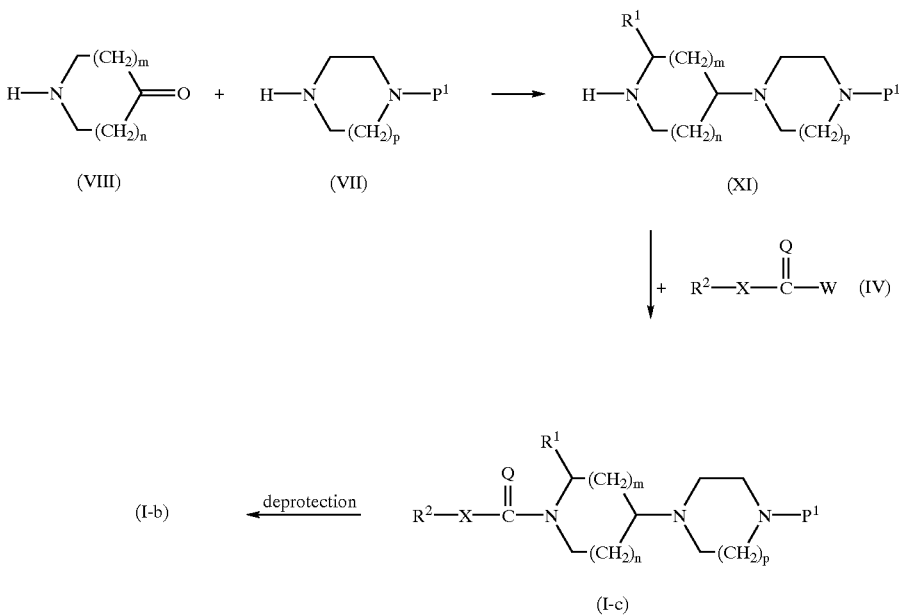

The compounds of formula (I-b) are deemed to be of particular use in the synthesis of other compounds of formula (I).

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For example, intermediates of formula (III), (IV) and (VI) may be prepared according to art-known procedures.

Intermediates of formula (II) may be prepared by condensing an intermediate of formula (IV) with an intermediate of formula (VIII) analogous to the procedure described in EP-0,532,456-A.

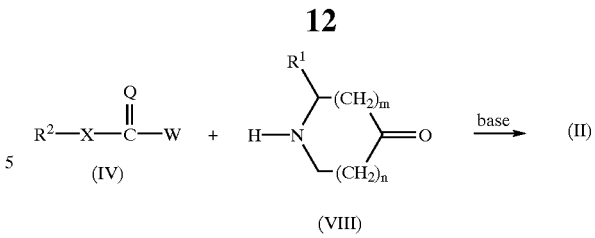

The preparation of intermediates of formula (VIII) is also described in EP-0,532,456-A. However, intermediates of formula (VIII) wherein $R^1$ is optionally substituted $Ar^1C_{1-6}$alkyl or di($Ar^1$)$C_{1-6}$alkyl, said $R^1$ being represented by —CH($R^{1a}$)$_2$ and said intermediates being represented by formula (VIII-a), may also be prepared as depicted in scheme 1.

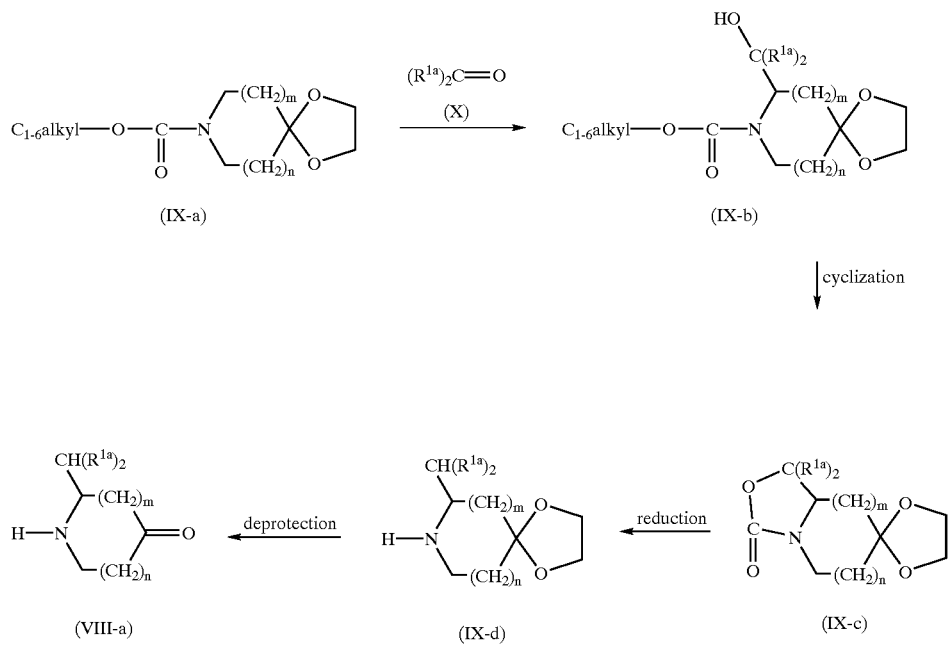

In scheme 1, the intermediates of formula (IX-b) may be prepared by reacting an intermediate of formula (IX-a) with an aldehyde or a ketone of formula (X). The $C_{1-6}$alkylcarbamate moiety in the intermediates of formula (IX-b) may be converted into a fused oxazolone which in turn may be reduced to an intermediate of formula (IX-d). Said intermediate (IX-d) may in turn be deprotected, thus forming an intermediate of formula (VIII-a). Subsequently, intermediates of formula (VIII-a) may be reacted with an intermediate of formula (IV) to prepare intermediates of formula (II) wherein $R^1$ is defined as —CH($R^{1a}$)$_2$, said intermediates being represented by formula (II-a).

Said intermediates of formula (II-a) may also be prepared by first reacting intermediate (IX-d) with intermediate (IV) in the presence of a suitable base to form an intermediate of formula (XII), which may subsequently be deprotected. These reactions and those performed in scheme 1 may all be conducted following conventional methods that are generally known in the art.

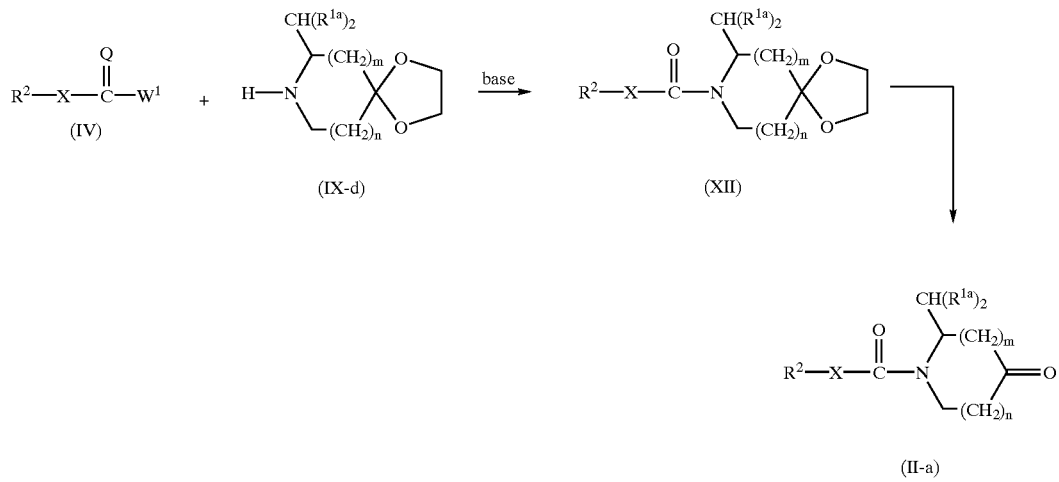

Intermediates of formula (V) may suitably be prepared by reacting an intermediate of formula (VIII-1), being a protected intermediate of formula (VIII) with a protecting group $P^2$ such as, for example, a $C_{1-6}$alkyloxycarbonyl group, with an intermediate of formula (III) according to the previously described reductive N-alkylation procedure, and subsequently deprotecting the thus formed intermediate.

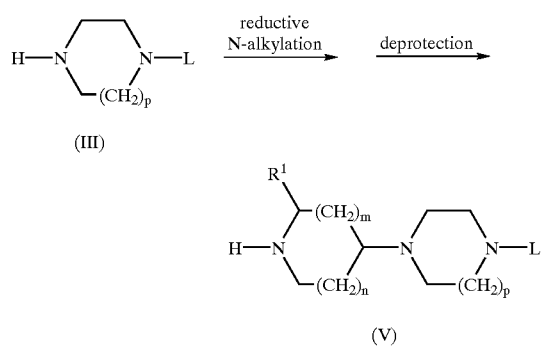

In particular, intermediates of formula (V) wherein $R^1$ is $-CH(R^a)_2$, said intermediates being represented by formula (V-a), may be prepared as is depicted in scheme 2.

Scheme 2

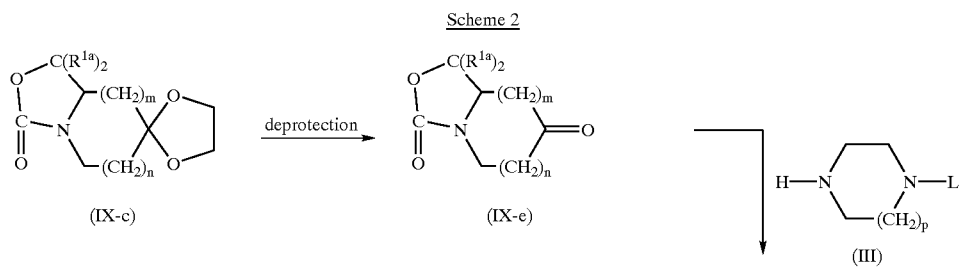

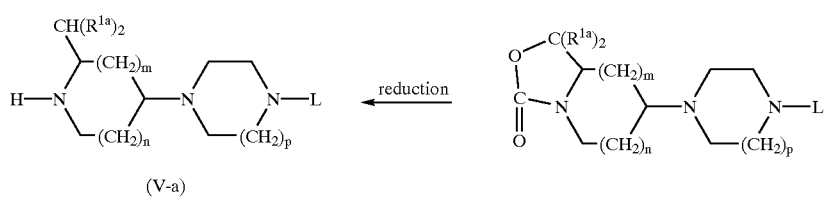

The ketalized intermediate of formula (IX-c) may be transformed to the corresponding ketone of formula (IX-e) which subsequently may be reductively aminated with a piperazine- or homopiperazine derivative of formula (III). The thus obtained intermediate may then be reduced with a suitable reducing agent to an intermediate of formula (V-a).

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) have valuable pharmacological properties in that they interact with tachykinin receptors and they antagonize tachykinin-induced effects, especially substance P-induced effects, both in vivo and in vitro and are thus of use in the treatment of tachykinin-mediated diseases, and in particular in substance P-mediated diseases.

Tachykinins, also referred to as neurokinins, are a family of peptides among which substance P (SP), neurokinin A (NKA), neurokinin B (NKB) and neuropeptide K (NPK) may be identified. They are naturally occurring in mammals, including human beings, and are distributed throughout the central and peripheral nervous system, where they act as neurotransmitters or neuromodulators. Their actions are mediated through several subtypes of receptors, such as, for example, $NK_1$, $NK_2$ and $NK_3$ receptors. Substance P displays highest affinity for $NK_1$ receptors, whereas NKA preferentially binds to $NK_2$ receptors and NKB preferentially binds to $NK_3$ receptors. However, the selectivity of these tachykinins is relatively poor and under physiological conditions the action of any of these tachykinins might be mediated by activation of more than one receptor type.

Substance P and other neurokinins are involved in a variety of biological actions such as pain transmission (nociception), neurogenic inflammation, smooth muscle contraction, plasma protein extravasation, vasodilation, secretion, mast cell degranulation, and also in activation of the immune system. A number of diseases are deemed to be engendered by activation of neurokinin receptors, in particular the $NK_1$ receptor, by excessive release of substance P and other neurokinins in particular cells such as cells in the neuronal plexi of the gastrointestinal tract, unmyelinated primary sensory afferent neurons, sympathetic and parasympathetic neurons and nonneuronal cell types (DN&P 8(1), February 1995, p. 5–23, "Neurokinin Receptors" by Longmore J. et al.; Pharmacological Reviews 46(4), 1994, p. 551–599, "Receptors and Antagonists for Substance P and Related Peptides" by Regoli et al.).

The compounds of the present invention are potent inhibitors of neurokinin-mediated effects, in particular those mediated via the $NK_1$ receptor, and may therefore be described as tachykinin antagonists, especially as substance P antagonists, as indicated in vitro by the antagonism of substance P-induced relaxation of pig coronary arteries which is described hereinafter. The binding affinity of the present compounds for the human, guinea-pig and gerbil neurokinin receptors may be determined in vitro in a receptor binding test using $^3$H-substance-P as radioligand. The subject compounds also show substance-P antagonistic activity in vivo as may be evidenced by, for instance, the antagonism of substance P-induced plasma extravasation in guinea-pigs, or the antagonism of drug-induced emesis in ferrets (Watson et al., Br. J. Pharmacol. 115, 84–94, 1995).

In view of their capability to antagonize the actions of tachykinins by blocking the tachykinin receptors, and in particular antagonizing the actions of substance P by blocking the $NK_1$ receptor, the subject compounds are useful in the prophylactic and therapeutic treatment of tachykinin-mediated diseases such as, for example, pain, in particular traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS-related neuropathy, occipital neuralgia, geniculate neuralgia, glossopharyngeal neuralgia, reflex sympathetic dystrophy, phantom limb pain; various forms of headache such as migraine, acute or chronic tension headache, temperomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; bums; scar pain; itch; and thalamic pain such as post stroke thalamic pain;

respiratory and inflammatory diseases, in particular inflammation in asthma, influenza, chronic bronchitis and rheumatoid arthritis; inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation;

emesis, i.e. nausea, retching and vomiting, including acute emesis, delayed emesis and anticipatory emesis, no matter how emesis is induced, for example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Ménière's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia;

central nervous system disorders, in particular psychoses such as schizophrenia, mania, dementia or other cognitive disorders e.g. Alzheimer's disease; anxiety; AIDS-related dementia; diabetic neuropathy; multiple sclerosis; depression; Parkinson's disease; and dependence on drugs or substances of abuse;

allergic disorders, in particular allergic disorders of the skin such as urticaria, and allergic disorders of the airways such as rhinitis;

gastrointestinal disorders, such as irritable bowel syndrome;

skin disorders, such as psoriasis, pruritis and sunburn;

vasospastic diseases, such as angina, vascular headache and Reynaud's disease;

cerebral ischaemia, such as cerebral vasospasm following subarachnoid haemorrhage;

stroke, epilepsie, head trauma, spinal cord trauma and ischemic neuronal damage;

fibrosing and collagen diseases, such as scleroderma and eosinophilic fascioliasis;

disorders related to immune enhancement or suppression, such as systemic lupus erythematosus;

rheumatic diseases, such as fibrositis;

neoplastic disorders;

cell proliferation; and cough.

The compounds of the present invention have a favourable metabolic stability and exhibit good oral availability. They also have an advantageous onset and duration of action. The compounds of formula (I) also have the ability to penetrate the central nervous system as may be demonstrated in vivo by their inhibitory effect on the change in behaviour induced by intracerebroventricular-applied substance P in the gerbil.

In view of the utility of the compounds of formula (I), there is provided a method of treating warm-blooded animals, including humans, suffering from tachykinin-mediated diseases as mentioned hereinabove, in particular, pain, emesis or asthma. Said method comprises the systemic administration of an effective tachykinin antagonizing amount of a compound of formula (I), a N-oxide form, a pharmaceutically acceptable addition salt or a possible stereoisomeric form thereof, to warm-blooded animals, including humans. Hence, the use of a compound of formula (I) as a medicine is provided, and in particular a medicine to treat pain, emesis or asthma.

For ease of administration, the subject compounds may be formulated into various pharmaceutical forms for administration purposes. To prepare the pharmaceutical compositions of this invention, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid or base addition salts of compounds of formula (I) due to their increased water solubility over the corresponding base or acid form, are obviously more suitable in the preparation of aqueous compositions.

In order to enhance the solubility and/or the stability of the compounds of formula (I) in pharmaceutical compositions, it can be advantageous to employ α-, β- or γ-cyclo-dextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in the treatment of tachykinin mediated diseases could determine the effective therapeutic daily amount from the test results presented hereinafter. An effective therapeutic daily amount would be from about 0.001 mg/kg to about 40 mg/kg body weight, more preferably from about 0.01 mg/kg to about 5 mg/kg body weight. It may be appropriate to administer the therapeutically effective dose once daily or as two, three, four or more sub-doses at appropriate intervals throughout the day. Said sub-doses may be formulated as unit dosage forms, for example, containing 0.05 mg to 500 mg, and in particular, 0.5 mg to 50 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.

The following examples are intended to illustrate and not to limit the scope of the present invention.

EXPERIMENTAL PART

Hereinafter "RT" means room temperature, "THF" means tetrahydrofuran, "DIPE" means diisopropylether, "DCM" means dichloromethane and "DMF" means N,N-dimethylformamide.

A. PREPARATION OF THE INTERMEDIATE COMPOUNDS

EXAMPLE A.1 a) A mixture of (±)-1,1-dimethyl 7-(phenylmethyl)-1,4-dioxa-8-azaspiro[4,5]decane-8-carboxylate (13 g; prepared according to the method described in EP-A-532,456) in HCl (6N; 130 ml) was stirred and refluxed for 3 hours. The reaction mixture was cooled, alkalized with aqueous NaOH (50%) and extracted with DCM. The organic layer was separated, dried, filtered, and the filtrate, which contained (±)-2-(phenylmethyl)-4-piperidinone (intermediate 1), was used in next reaction step.

b) A mixture of the filtrate obtained in the previous reaction step, 3,5-dimethylbenzoyl chloride (7.4 g) and triethylamine (11 ml) was stirred overnight at RT. The reaction mixture was extracted with dilute NaOH solution. The organic layer was separated, dried, filtered and the solvent evaporated. The residue was crystallized from DIPE. The precipitate was filtered off and dried, yielding 7.44 g (58%) of (±)-1-(3,5-dimethyl-benzoyl)-2-(phenylmethyl)-4-piperidinone (intermediate 2; mp. 107.8° C.).

EXAMPLE A.2 a) A mixture of (±)-1,1-dimethyl 7-(phenylmethyl)-1,4-dioxa-8-azaspiro[4,5]decane-8-carboxylate (33.34 g; prepared according to the method described in EP-A-532,456) in HCl (6N; 250 ml) was stirred at 70° C. for 1 hour and 30 minutes. The mixture was cooled, alkalized with NaOH while cooling to 25° C., and extracted with DCM (100 ml). The organic layer was separated and the aqueous layer was extracted with $CH_2Cl_2$. Triethylamine (20.2 g), followed by 3,5-bis(trifluoromethyl)benzoyl chloride (27.7 g) dissolved in a little DCM were added and the mixture was stirred for 2 hours. The mixture was extracted with water, and the layers were separated. The organic layer was dried, filtered and the solvent evaporated. The residue was crystallized from DIPE, the precipitate was filtered off and dried, yielding 18.34 g product. The mother layer was evaporated and the residue was crystallized from DIPE. The precipitate was filtered off and dried, yielding 6.51 g of product. The two fractions were put together and taken up in water and DCM, NaOH was added and the mixture was extracted. The organic layer was dried, filtered and the solvent evaporated, yielding 16.14 g (38%) of (±)-1-[3,5-bis(trifluoromethyl)benzoyl]-2-(phenylmethyl)-4-piperidinone (intermediate 3; mp.t02.5° C.).

EXAMPLE A.3

A mixture of pyrrolidine (2.13 g) and triethylamine (6.06 g) in DCM (100 ml) was stirred at −10° C. 2-chloro-2-phenylacetylchloride (5.67 g) was added slowly and dropwise. The mixture was allowed to warm to RT and was then stirred overnight. The mixture was extracted with water and $K_2CO_3$. The separated organic layer was dried, filtered and the solvent was evaporated. The residue was crystallized from DIPE and the precipitate was filtered off and dried, yielding 3.25 g (48%) of fraction 1. The mother layer was separated and the solvent was evaporated. The residue was crystallized from DIPE and the precipitate was filtered off and dried, yielding 0.29 g (5%) of fraction 2. Both fractions were combined, thus yielding 3.54 g (53%) of (±)-1-(2-chloro-2-phenylacetyl)pyrrolidine (intermediate 4; mp. 88.5° C.).

EXAMPLE A.4

Sodium hydride (2 g) was added portionwise to a solution of 3,5-dimethylphenol (6.1 g) in DMF (50 ml). The mixture was stirred for 30 minutes and added dropwise at a temperature below 30° C. to a solution of 2-chloro-2-phenylacetylchloride (9.45 g) in DMF (50 ml). The mixture was stirred overnight, decomposed with water (5 ml) and the solvent was evaporated. Water was added and the mixture was extracted with DCM. The separated organic layer was dried, filtered and the solvent was evaporated. The residue was purified over silica gel on a glass filter (eluent: hexane/DIPE 100/0, 98/2 and 95/5). The pure fractions were collected and the solvent was evaporated [residue; yielding 10.82 g (79%)]. A small amount of the obtained residue was crystallized from DIPE, the precipitate was filtered off and the solvent was evaporated, yielding 1 g of (±)-3,5-dimethylphenyl α-chlorobenzeneacetate (intermediate 5; mp. 79.0° C.).

EXAMPLE A.5 a) A mixture of (±)-1-[3,5-bis(trifluoromethyl)benzoyl]-2-(phenylmethyl)-4-(1-piperazinyl)piperidine (0.0127 mol), chloroacetonitrile (0.013 mol) and sodium carbonate (0.013 mol) in methylisobutyl keton (100 ml) was stirred and refluxed. The mixture was cooled and water was added. The organic layer was separated, dried, filtered and the solvent was evaporated. The residue was purified over silica gel on a glass filter (eluent: $CH_2Cl_2/CH_3OH$ 100/0, 99.5/0.5 and 99/1). The pure fractions were collected and the solvent was evaporated, yielding 3.64g (53%) of (±)-cis-1-[3,5-bis-(trifluoromethyl)benzoyl]-4-[4-(cyanomethyl)-1-piperazinyl]-2-(phenylmethyl) piperidine (intermediate 6).

b) A mixture of intermediate 6 (0.0067 mol) in THF (150 ml) was hydrogenated at 20° C. with Raney Nickel (1 g) as a catalyst. After uptake of hydrogen, the catalyst was filtered off and the filtrate was evaporated, yielding 3.77 g of (±)-cis-4-[4-(2-aminoethyl)-1-piperazinyl]-1-[3,5-(trifluoromethyl)benzoyl]-2-(phenylmethyl)piperidine (intermediate 7).

EXAMPLE A.6

A mixture of 1-(phenylmethyl)-4-piperidinone (0.2 mol) and 1-methylpiperazine (0.2 mol) in methanol (500 ml) was hydrogenated for 8 hours with palladium on activated carbon (10%, 2.5 g) as a catalyst. After uptake of hydrogen, the catalyst was filtered off and the filtrate was evaporated. A mixture of di-tert -butyl dicarbonate (0.2 mol) in THF (500 ml) was added to the residue and hydrogenated again with palladium on activated carbon (10%, 2.5 g) as a catalyst. After uptake of hydrogen, the catalyst was filtered off and the filtrate was evaporated. The residue was purified over silica gel on a glass filter (eluent: $CH_2Cl_2/CH_3OH$ 95/5). The pure fractions were collected and the solvent was evaporated, yielding 45.3 g (80%) of 1,1-dimethylethyl 4-(4-methyl-1-piperazinyl)-1-piperidinecarboxylate (intermediate 8).

EXAMPLE A.7 a) A mixture of 4-methoxypyridine (0.4 mol) in THF (1000 ml) was stirred and cooled in a 2-propanol/$CO_2$ bath. Ethyl chloroformate (0.4 mol) was added dropwise and the mixture was stirred for 3 hours while cooling (mixture I). In another round-bottom flask, the Grignard-reagent was prepared: Mg (0.44 mol) was stirred in a small amount of $(C_2H_5)_2O$. Some 12 was added. A small amount of 1,2-dichloro-4-(chloromethyl)-benzene was added. Then, 1,2-dichloro-4-(chloromethyl)benzene (0.4 mol) in $(C_2H_5)_2O$ (600 ml) was added dropwise at reflux temperature. The mixture was stirred for one hour (mixture II). The Grignard-reagent was decanted off, added to mixture I at <−40° C., and the resulting reaction mixture was stirred, allowing the temperature to reach RT. The reaction mixture was stirred for one hour at RT. HCl (10%, 800 ml) was added and the mixture was stirred for 30 minutes, then $CH_2Cl_2$ was added. The organic layer was separated, dried, filtered and the solvent evaporated, yielding 57.8 g (44%) of (±)-ethyl 6-[(3,4-dichlorophenyl)methyl]-1,2,3,4-tetrahydro-4-oxo-1-pyridinecarboxylate (intermediate 9).
b) Intermediate 9 (0.176 mol) in THF (880 ml) was stirred under a $N_2$ flow, and cooled to −78° C. L-selectride (0.264 mol) was added dropwise at −78° C. The reaction mixture was stirred for 1 hour, then poured out into water. DIPE was added. The organic layer was separated, washed with an aqueous $NaHCO_3$ solution, with an aqueous NaCl solution, dried, filtered and the solvent was evaporated. The residue was purified by column chromatography over silica gel (eluent: $CH_2Cl_2/CH_3OH$ 90/10). The desired fractions were collected and the solvent was evaporated, yielding 20.2 g (34.8%) of (±)-ethyl 2-[(3,4-dichlorophenyl)methyl]-4-oxo-1-piperidinecarboxylate (intermediate 10).
c) Titanium(IV)isopropoxide (0.0269 mol) was added to a mixture of intermediate 10 (0.0224 mol) and intermediate 10 (0.0224 mol) in DCM (11 ml). The mixture was stirred at RT for 3 hours. Sodium cyanoborohydride (0.0224 mol) and then ethanol (10 ml) were added. The mixture was stirred at RT for 48 hours. Water was added and the mixture was stirred. $CH_2Cl_2$ was added and the mixture was stirred. The organic layer was separated, dried, filtered and the solvent was evaporated. The residue was purified by HPLC over silica gel (eluent: $CH_2Cl_2/CH_3OH$ 100/0 and 98/2). The pure fractions were collected and the solvent was evaporated. The residue was purified by reversed phase chromatography (eluent: $NH_4OAc$(0.5% in $H_2O$)/$CH_3OH$ 20/80). Two pure fractions were collected and their solvents were evaporated. The residue was dried and ground, yielding 2 g (16%) of (±)-ethyl trans-2-[(3,4-dichlorophenyl)methyl]-4-[4-[2-[(2,6-dimethylphenyl)amino]-2-oxoethyl]-1-piperazinyl]-1-piperidinecarboxylate (intermediate 11) and 3.5 g (28%) of (±)-ethyl cis-2-[(3,4-dichlorophenyl)methyl]-4-[4-[2-[(2,6-dimethylphenyl)amino]-2-oxoethyl]-1-piperazinyl]-1-piperidinecarboxylate (intermediate 12).
d) A mixture of intermediate 11 (0.0034 mol) and potassium hydroxide (0.034 mol) in 2-propanol (150 ml) was stirred and refluxed for 4 days. The solvent was evaporated. The residue was taken up in $CH_2Cl_2$/water. The organic layer was separated, dried, filtered and the solvent was evaporated. The residue was purified by column chromatography over silica gel (eluent: $CH_2Cl_2/(CH_3OH/NH_3)$ 95/5). The pure fractions were collected and the solvent was evaporated, yielding 0.5 g (30%) of (±)-trans-4-[2-[(3,4-dichlorophenyl)methyl]-4-piperidinyl]-N-(2,6-dimethylphenyl)-1-piperazineacetamide (intermediate 13).

EXAMPLE A.8 a) Sec-butyllithium (0.066 mol) was added to a mixture of 1,1-dimethylethyl 1,4-dioxo-8-azaspiro[4.5]-8-carboxylate (0.06 mol) in N,N,N',N'-tetramethylethylenediamine (22.6 ml) and $(C_2H_5)_2O$ (100 ml). The mixture was stirred at −70° C. for 3 hours. 3,5-difluorobenzaldehyde (0.07 mol) was added dropwise at −70° C. The mixture was allowed to warm to RT. Water (50 ml) and DIPE were added. The aqueous layer was separated and extracted with $CH_2Cl_2$. The combined organic layer was dried, filtered and the solvent was evaporated. Toluene was added and evaporated again, yielding 23 g of (±)-1,1-dimethylethyl 7-[(3,5-difluorophenyl)-hydroxymethyl]-1,4-dioxo-8-azaspiro [4.5]-8-carboxylate (intermediate 14).
b) A mixture of intermediate 14 (0.06 mol) and 2-methyl-2-propanol, potasssium salt (0.72 g) in toluene (110 ml) was stirred and refluxed for 2 hours. The solvent was evaporated. The residue was stirred in petroleum ether and a small amount of water, and decanted. The residue was dissolved in $CH_2Cl_2$, dried, filtered and the solvent was evaporated. The residue was purified by column chromatography over silica gel (eluent: $CH_2Cl_2/CH_3OH$ 100/0, 99/1 and 98/2). Two pure fractions were collected and their solvents were evaporated, yielding 9.2 g (49%) of (±)-3-(3,5-difluorophenyl)tetrahydrospiro[1,3-dioxolan-2,5'(3'H)-1H-oxazolo[3,4-a]pyridin]-1-one (intermediate 15).
c) A mixture of intermediate 15 (0.03 mol) in methanol (250 ml) was hydrogenated at 50° C. with palladium on activated carbon (10%, 2 g) as a catalyst. After uptake of hydrogen, the catalyst was filtered off and the filtrate was evaporated. The residue was purified over silica gel on a glass filter (eluent: $CH_2Cl_2/CH_3OH$ 100/0, 98/2 and 95/5 and $CH_2Cl_2/(CH_3OH/NH_3)$ 95/5). The desired fractions were collected and the solvent was evaporated, yielding 1.9 g (39%) of (±)-7-[(3,5-difluorophenyl)methyl]-1,4-dioxo-8-azaspiro[4.5]decane (intermediate 16).
d) A mixture of intermediate 16 (0.012 mol) in HCl 6N (30ml) was stirred at 75° C. for 2 hours. The mixture was cooled, poured out into ice and a NaOH solution and extracted with CH₂Cl₂. The organic layer was separated, dried and filtered, yielding 2.7 g of (±)-2-[(3,4-difluorophenyl)methyl]-4-piperidinone (intermediate 17).

e) A mixture of 3,5-trifluoromethylbenzoyl chloride (0.012 mol) in a small amount of CH₂Cl₂ was added dropwise to a stirred mixture of intermediate 17 (0.012 mol) and N,N-diethylethanamine (0.024 mol). The mixture was stirred at RT for 1 hour and water was added. The organic layer was separated, dried, filtered and the solvent was evaporated. The residue was purified over silica gel on a glass filter (eluent: CH₂Cl₂/CH₃OH 100/0 and 99.5/0.5). The pure fractions were collected and the solvent was evaporated, yielding 2.7 g (48%) of (±)-1-[3,5-bis(trifluoromethyl)benzoyl]-2-[(3,5-difluorophenyl)methyl]-4-piperidinone (intermediate 18).

EXAMPLE A.9

Sec-butyllithium (0.63 mol) was added at −78° C. under N₂ flow to a solution of 1,1-dimethylethyl 1,4-dioxo-8-azaspiro[4.5]-8-carboxylate (0.57 mol) and N,N,N'N'-tetramethylethylenediamine (1.14 mol) in (C₂H₅)₂O (1000 ml). One hour after complete addition, a mixture of 3-(trifluoromethyl)benzaldehyde (0.57 mol) in (C₂H₅)₂O (200 ml) was added. The mixture was allowed to warm to RT and then stirred at RT for 16 hours. The solvent was evaporated. A mixture of 2-methyl-2-propanol, potassium salt (0.2 mol) in toluene (500 ml) was added. The mixture was stirred at 80° C. for 5 hours. The solvent was evaporated. The residue was heated with a saturated NH₄Cl solution and extracted with CH₂Cl₂. The organic layer was separated, dried and the solvent was evaporated. The residue was suspended in DIPE, filtered off and dried. This fraction was dissolved in CH₃OH (250 ml) and the mixture was hydrogenated with palladium on activated carbon (10%, 3 g) as a catalyst. After uptake of hydrogen, the catalyst was filtered off and the filtrate was evaporated. The residue was purified over silica gel on a glass filter (eluent: CH₂Cl₂/CH₃OH 95/5). The pure fractions were collected and the solvent was evaporated. This fraction was dissolved in HCl (6N, 100 ml) and CH₃OH (100 ml) and the mixture was stirred at 50° C. for 8 hours. The organic solvent was evaporated. The concentrate was washed with a saturated K₂CO₃ solution and extracted with CH₂Cl₂. The organic layer was separated, dried, filtered and the solvent was evaporated. The residue was purified over silica gel on a glass filter (eluent: CH₂Cl₂/CH₃OH 95/5). The pure fractions were collected and the solvent was evaporated, yielding 48.5 g (70%) of (±)-2-[[4-(trifluoromethyl)phenyl]methyl]-4-piperidinone (intermediate 19).

EXAMPLE A.10 a) A mixture of ethyl β-oxobenzenebutanoate (0.5 mol) and benzenemethanamine (0.5 mol) in toluene (500 ml) was hydrogenated at 120° C. (pressure=100 kg) overnight in the presence of Cu₂Cr₂O₅ (5 g) and CaO (10 g). After uptake of hydrogen, the catalyst was filtered off and the filtrate was evaporated, yielding 29.7 g of (±)-ethyl N,2-bis(phenylmethyl)-β-alanine (intermediate 20).

b) Ethyl chloroacetate (0.3 mol) was added to a mixture of intermediate 20 (0.2 mol) in DMF (250 ml). The mixture was stirred and triethylamine (0.4 mol) was added. The mixture was stirred at 60° C. overnight. The solvent was evaporated and the residue was taken up in water/CH₂Cl₂. The organic layer was separated, dried, filtered and the solvent was evaporated, yielding 76.6 g of (±)-ethyl 3-[(2-ethoxy-2-oxoethyl)(phenyl-methyl)amino]benzenebutanoate (intermediate 21).

c) Intermediate 21 (0.2 mol) was heated to 80° C. under N₂ flow. NaOCH₃ (44 g) was added. The mixture was stirred at 80° C. for 30 minutes. The solvent was evaporated and water (170 ml) and HCl (6N, 60 ml) were added. The mixture was stirred and refluxed for 1 hour, then cooled, alkalized with NaOH and extracted with CH₂Cl₂. The organic layer was separated, washed with water and a saturated NaCl solution, dried, filtered and the solvent was evaporated. The residue was purified by column chromatography over silica gel (eluent: CH₂Cl₂/CH₃CN 100/0 to 96/4). The pure fractions were collected and the solvent was evaporated, yielding 7.8 g of (±)-1,5-bis(phenylmethyl)-3-pyrrolidinone (intermediate 22).

d) A mixture of intermediate 22 (0.027 mol) and CH₃SO₃H (0.03 mol) in THF (200 ml) was hydrogenated with palladium on activated carbon (10%, 2 g) as a catalyst. After uptake of hydrogen, the catalyst was filtered off, yielding (±)-5-(phenylmethyl)-3-pyrrolidinone methanesulfonate(1:1) (intermediate 23).

e) 3,5-di(trifluoromethyl)benzoyl chloride (0.03 mol) was added to intermediate 23 (0.027 mol). The mixture was stirred and triethylamine (0.1 mol) was added. The mixture was stirred at RT for 18 hours and then washed with water, NaOH and a saturated NaCl solution. The organic layer was separated, washed with a saturated NaCl solution, dried, filtered and the solvent was evaporated. The residue was purified by column chromatography over silica gel (eluent: CH₂Cl₂/CH₃OH 98/2). The pure fractions were collected and the solvent was evaporated, yielding 1.4 g of (±)-1-[3,5-bis(trifluoromethyl)benzoyl]-5-(phenylmethyl)-3-pyrrolidinone (intermnediate 24).

B. PREPARATIONS OF THE COMPOUNDS OF FORMULA (I)

EXAMPLE B.1 a) Titanium(IV)isopropoxide (16.5 g) was added to a mixture of intermediate 3 (21.5 g) and 1-(phenylmethyl)piperazine (8.81 g) in DCM (35 ml). The mixture was stirred for 3 hours at RT. Sodium cyanoborohydride (2.85 g) and ethanol (70 ml) were added and the resulting reaction mixture was stirred overnight at RT. Water (5 ml) and DCM were added. The biphasic mixture was filtered over dicalite, and the filter residue was washed with DCM. The organic layer was separated, dried, filtered and the solvent was evaporated. The residue was crystallized from CH₃CN and the precipitate was filtered off and dried, yielding 7.93 g (26.9%) of (±)-cis-1-[3,5-bis(trifluoromethyl)benzoyl]-2-(phenylmethyl)-4-[4-(phenylmethyl)-1-piperazinyl]piperidine (compound 16; mp. 143.8° C.).

b) The mother liquor was concentrated and the residue was purified by column chromatography over silica gel (eluent: CH₂Cl₂/CH₃OH 100/0, then 99/1, 98/2, 97/3). The desired fractions ((A) and (B)) were collected and their solvent was evaporated. The A-isomer was crystallized from CH₃CN, filtered off and dried, yielding 1.11 g (4%) of compound 16. The pure fractions of the B-isomer were concentrated, yielding 5.9 g (20%) of (±)-trans-1-[3,5-bis(trifluoromethyl)benzoyl]-2-(phenylmethyl)-4-[4-(phenylmethyl)-1-piperazinyl]piperidine. The impure fractions of the B-isomer were collected and the solvent was evaporated. The residue was converted into the fumaric acid salt (1:2) in ethanol. The precipitate was filtered off and dried, yielding 1.89 g (±)-trans-1-[3,5-bis(trifluoromethyl)benzoyl]-2-(phenylmethyl)-4-[4-(phenylmethyl)-1-piperazinyl]piperidine (E)-2-butenedioate(1:2) (compound 17; mp. 240.3° C.).

EXAMPLE B.2

A mixture of compound 16 (8.4 g) in methanol (250 ml) was hydrogenated at 50° C. with palladium on activated carbon (10%) (2 g) as a catalyst. After uptake of H$_2$, the catalyst was filtered off and the filtrate was evaporated, yielding 7 g (100%) of (±)-1-[3,5-bis(trifluoromethyl) benzoyl]-2-(phenylmethyl)-4-(1-piperazinyl)piperidine (compound 15).

EXAMPLE B.3 a) Titanium(IV)isopropoxide (13.2 g) was added to a mixture of intermediate 3 (17.16 g) and N-(2,6-dimethylphenyl)-1-piperazineacetamide (9.88 g) in DCM (20 ml). This mixture was stirred for 3 hours at RT. Sodium cyanoborohydride (2.52 g) in ethanol (20 ml) was added and the resulting reaction mixture was stirred overnight at RT. Water (10 ml) was added and the reaction mixture was extracted with DCM (800 ml). The organic layer was separated, dried, filtered and the solvent was evaporated. The residue was taken up into water and this mixture was extracted with DCM. The separated organic layer was dried, filtered, and the solvent evaporated. The residue was pre-purified by column chromatography over silica gel (eluent: CH$_2$Cl$_2$/CH$_3$OH 97/3). The desired fractions were collected and the solvent was evaporated, giving 4 g of the trans-racemate. Resolution was obtained by purification over stationary phase Chiralcel OD (eluent: CH$_3$OH 100%). Two desired trans-fraction groups were collected and their solvent was evaporated, yielding 1.75 g fraction 1 and 2 g fraction 2. Fraction 1 was dissolved in DCM, filtered and the filtrate was evaporated. The residue was dried, yielding 1.55 g (6%) (±)-(A)-trans-4-[1-[3,5-bis(trifluoromethyl)benzoyl]-2-(phenyl-methyl)-4-piperidinyl]-N-(2,6-dimethylphenyl)-1-piperazine acetamide (compound 26; mp. 97.4° C.; $[\alpha]_D^{20}$=−5.81° (c=1% in DMF)). Fraction 2 was dissolved in DCM, filtered and the filtrate was evaporated. The residue was dried, yielding 1.70 g (6%) (±)-(B)-trans-4-[1-[3,5 -bis(trifluoromethyl)benzoyl]-2-(phenylmethyl)-4-piperidinyl]-N-(2,6-dimethylphenyl)-1-piperazine acetamide (compound 27; mp. 96.8° C.; $[\alpha]_D^{20}$=+5.71° (c=1% in DMF)).

b) Compound 27 was dissolved in warm 2-propanol and converted into the (L)-malic acid salt with a solution of (L)-malic acid in 2-propanol. The mixture was stirred for 2 hours and the precipitate was filtered off and dried, yielding (±)-(B)-trans-4-[1-[3,5-bis(trifluoromethyl) benzoyl]-2-(phenylmethyl)-4-piperidinyl]-N-(2,6-dimethylphenyl)-1-piperazine acetamide (L)-malic acid (1:1) (compound 95).

EXAMPLE B.4

A mixture of compound 15 (2.5 g), intermediate 5 (1.65 g) and sodium carbonate (0.64 g) in methylisobutylketon (50 ml) was stirred and refluxed for 3 hours. The reaction mixture was washed and the separated organic layer was dried, filtered and the solvent was evaporated. The residue was purified over silica gel on a glass filter (eluent: CH$_2$Cl$_2$/CH$_3$OH 100/0 and 99.5/0.5). The pure fractions were collected and the solvent was evaporated, yielding 1.59 g (43%) of (±)-3,5-dimethylphenyl cis-4-[1-[3,5-bis(trifluoromethyl) benzoyl]-2-(phenylmethyl)-4-piperidinyl]-α-phenyl-1-piperazineacetate (compound 43; mp. 88.1° C.).

EXAMPLE B.5

A mixture of intermediate 2 (3.2 g), 1-(diphenylmethyl) piperazine (2.5 g) and aluminum tributoxide (2 g) in toluene (250 ml) was hydrogenated for 48 hours at 50° C., with palladium on activated carbon (10%; 2 g) as a catalyst in the presence of thiophene (4% solution; 1 ml). After uptake of hydrogen (1 equiv), the catalyst was filtered off and the filtrate was evaporated. The residue was purified by high-performance liquid chromatography over silica gel (eluent: CH$_2$Cl$_2$/CH$_3$OH 100/0, upgrading to 90/10). Two pure fractions were collected and their solvent was evaporated, resulting in residue 1 and residue 2. Residue 1 was suspended in DIPE. The precipitate was filtered off and dried, yielding 0.94 g (17%) of (±)-cis-1-(dimethylbenzoyl)-4-[4-(diphenylmethyl)-1-piperazinyl]-2-(phenylmethyl) piperidine (compound 12; mp. 100.8° C.). Residue 2 was dried, yielding 0.2 g (3.6%) of (±)-trans-1-(dimethylbenzoyl)-4-[4-(diphenylmethyl)-1-piperazinyl]-2-(phenylmethyl)piperidine (compound 13).

EXAMPLE B.6

A mixture of compound 15 (0.005 mol) and 1,2-epoxyethylbenzene (0.006 mol) in methanol (50 ml) was stirred at RT for 1 hour. The mixture was stirred and refluxed for 3 hours. The solvent was evaporated and the residue was purified over silica gel on a glass filter (eluent: CH$_2$Cl$_2$/CH$_3$OH 100/0, 99/1 and 98/2). The pure fractions were collected and the solvent was evaporated. The residue was purified by HPLC over silica gel (eluent: CH$_2$Cl$_2$/CH$_3$OH 98/2 to 95/5). Two pure fractions were collected and their solvents were evaporated. Each residue was dried, yielding 0.7 g (23%) of (±)-cis-1-[3,5-bis(trifluoromethyl)benzoyl]-4-[4-(2-hydroxy-2-phenylethyl)-1-piperazinyl]-2-(phenylmethyl)piperidine (compound 60) and 0.23 g (7%) of (±)-cis-1-[3,5-bis(trifluoromethyl)benzoyl]-4-[4-(2-hydroxy-1-phenylethyl)-1-piperazinyl]-2-(phenylmethyl) piperidine (compound 61).

EXAMPLE B.7

Compound 15 (0.005 mol), 2-chloro-1-[(2-methyl-5-oxazolyl)methyl]-1H-benzimidazole (0.005 mol) and Cupper (0.005 mol) were stirred at 140° C. for 2 hours. The mixture was cooled, dissolved in CH$_2$Cl$_2$, filtered and washed with CH$_2$Cl$_2$ and a diluted NH$_4$OH solution. The organic layer was separated, washed with a diluted NH$_4$OH solution, dried, filtered and the solvent was evaporated. The residue was purified over silica gel on a glass filter (eluent: CH$_2$Cl$_2$/CH$_3$OH 100/0, 99.5/0.5, 99/1, 98.5/1.5 and 98/2). The pure fractions were collected and the solvent was evaporated. The residue was dried, yielding 1.42 g (40%) (±)-cis-1-[3,5-bis(trifluoromethyl)-benzoyl]-4-[4-[1-[(2-methyl-5-oxazolyl)methyl]-1H-benzimidazol-2-yl]-1-piperazinyl]-2-(phenylmethyl)piperidine (compound 70).

EXAMPLE B.8

A mixture of intermediate 7 (0.0033 mol) and 3,5-dimethylbenzoyl chloride (0.0035 mol) in DCM (50 ml) was stirred at RT for 15 minutes. Triethylamine (0.007 mol) was added and the mixture was stirred at RT for 1 hour. Water was added. The organic layer was separated, dried, filtered and the solvent was evaporated. The residue was converted into the fumaric acid salt (1:1) with 2-propanol. The precipitate was filtered off and dried. The residue was converted into the free base with NaOH. The precipitate was filtered off and dried. The residue was purified over silica gel on a glass filter (eluent: CH$_2$Cl$_2$/CH$_3$OH 100/0, 99.5/0.5, 99/1, 98/2 and 97/3). The pure fractions were collected and the solvent was evaporated. The residue was dried, yielding 0.8 g (36%) (±)-cis-N-[2-[4-[1-[3,5-bis(trifluoromethyl)benzoyl]-2-

(phenylmethyl)-4-piperidinyl]-1-piperazinyl]ethyl]-3,5-dimethylbenzamide (compound 116).

EXAMPLE B.9

A mixture of compound 74, prepared according to example B.4, (0.004 mol) in methanol (150 ml) was hydrogenated at 50° C. with palladium on activated carbon (10%; 1 g) as a catalyst in the presence of thiophene (4% solution, 1 ml). After uptake of hydrogen, the catalyst was filtered off and the filtrate was evaporated. The residue was crystallized from DIPE. The precipitate was filtered off, washed with DIPE and dried. This fraction was dissolved in toluene. The mixture was filtered and the solvent was evaporated. The residue was suspended in DIPE. The precipitate was filtered off and dried. This fraction was converted into the fumaric acid salt (1:2) with a warm solution of fumaric acid (0.52 g) in ethanol. The mixture was stirred for 6 hours. The precipitate was filtered off and dried, yielding 0.91 g (25%) of (±)-cis-N-(4-amino-2,6-dimethylphenyl)-4-[1-[3,5-(trifluoromethyl)benzoyl]-2-(phenylmethyl)-4-piperidinyl]-1-piperazineacetamide (E)-2-butenedioate(1:2) (compound 129).

EXAMPLE B.10

Sec-butyllithium (0.055 mol) was added at −78° C. under $N_2$ flow to a solution of 1,1-dimethylethyl 4-(4-methyl-1-piperazinyl)-1-piperidinecarboxylate (0.05 mol) and N,N,N',N'-tetramethylethylenediamine (0.1 mol) in $(C_2H_5)_2O$ (50 ml). 2 hours after complete addition, a mixture of benzaldehyde (0.05 mol) in $(C_2H_5)_2O$ (50 ml) was added. The mixture was allowed to warm to RT and then stirred at 25° C. for 16 hours. The solvent was evaporated and the residue was washed with a saturated $NH_4Cl$ solution and extracted with $CH_2Cl_2$. The organic layer was separated, dried, filtered and the solvent was evaporated. A solution of 2-methyl-2-propanol, potassium salt (0.02 mol) in toluene (100 ml) was added to this fraction and the mixture was stirred at 100° C. for 2 hours. The solvent was evaporated. The residue was washed with a saturated $NH_4Cl$ solution, extracted with $CH_2Cl_2$ and decanted. The organic layer was dried, filtered and the solvent was evaporated. The residue was purified over silica gel on a glass filter (eluent: $CH_2Cl_2$/$CH_3OH$ 95/5). The pure fractions were collected and the solvent was evaporated. This fraction was dissolved in methanol (150 ml) and hydrogenated with palladium on activated carbon (10%, 3 g) as a catalyst. After uptake of hydrogen, the catalyst was filtered off and the filtrate was evaporated. The residue was purified over silica gel on a glass filter (eluent: $CH_2Cl_2$/$CH_3OH$ 95/5). The pure fractions were collected and the solvent was evaporated. This fraction was dissolved in DCM (20 ml) and Triethylamine (2 ml). 3,5-di(trifluoromethyl)benzoyl chloride (0.0087 mol) was added at 0° C. 1 hour after complete addition, water was added and the mixture was extracted with $CH_2Cl_2$. The organic layer was separated, dried, filtered and the solvent was evaporated. The residue was purified over silica gel on a glass filter (eluent: $CH_2Cl_2$/$CH_3OH$ 95/5). The pure fractions were collected and the solvent was evaporated. This fraction was converted into the (E)-2-butenedioic acid salt (1:2) with ethanol. The precipitate was filtered off and dried, yielding 4.7 g (74%) of (±)-cis-1-[3,5-bis(trifluoromethyl)benzoyl]-4-(4-methyl-1-piperazinyl)-2-(phenylmethyl)piperidine (E)-2-butenedioate(1:2) (compound 130).

EXAMPLE B.11

A mixture of compound 15 (0.005 mol), N-[2-(3,4-dichlorophenyl)-4-[(methylsulfonyl)oxy]butyl]-N-methyl benzamide (0.0055 mol) and $NaHCO_3$ (0.0055 mol) in ethanol (50 ml) was stirred and refluxed for 6 hours. The solvent was evaporated, the residue was taken up in water and extracted with $CH_2Cl_2$. The organic layer was separated, dried, filtered and the solvent was evaporated. The residue was purified over silica gel on a glass filter (eluent: $CH_2Cl_2$/$CH_3OH$ 100/0, 99/1, 98/2 and 97/3). The pure fractions were collected and the solvent was evaporated. The residue was converted into the fumaric acid salt (1:2) with ethanol. The precipitate was filtered off and dried, yielding 1.42 g (27%) of (±)-cis-N-[4-[4-[1-[3,5-bis(trifluoromethyl)benzoyl]-2-(phenylmethyl)-4-piperidinyl]-1-piperazinyl]-2-(3,4-dichlorophenyl)butyl]-N-methylbenzamide (E)-2-butenedioate(1:2) (compound 93).

EXAMPLE B.12

A mixture of (±)-1-[3,5-bis(trifluoromethyl)benzoyl]-2-[(3,5-difluorophenyl)methyl]-4-piperidinone (0.0058 mol), N-(2,6-dimethylphenyl)-1-piperazineacetamide (0.0058 mol) and titanium(IV)isopropoxide (0.0064 mol) in 2-propanol (5 ml) was stirred at RT overnight. $NaBH_4$ (0.0116 mol) and ethanol (15 ml) were added. The mixture was stirred for 2 days. Water (5 ml) was added and the mixture was stirred for 10 minutes. $CH_2Cl_2$ (200 ml) was added. The organic layer was separated, dried, filtered and the solvent was evaporated. This fraction was purified by HPLC over silica gel (eluent: $CH_2Cl_2$/$CH_3OH$ 98/2 to 90/10 over a 30-minute period). Two pure fractions (F1 and F2) were collected and their solvents were evaporated. F1 was purified by column chromatography over RP18 (eluent: $NH_4OAc$ (0.5% in $H_2O$)/$CH_3CN$ 40/60). The pure fractions were collected and the solvent was evaporated. The residue was dried, yielding 0.33 g (8%) of (±)-cis-4-[1-[3,5-bis(trifluoromethyl)benzoyl]-2-[(3,5-difluorophenyl)methyl]-4-piperidinyl]-N-(2,6-dimethylphenyl)-1-piperazineacetamide (compound 132). F2 was purified by column chromatography over silica gel (eluent: $CH_2Cl_2$/$CH_3OH$ 100/0 to 92/8 over a 30-minute period). The pure fractions were collected and the solvent was evaporated. The residue was dissolved in $CH_2Cl_2$, filtered and the solvent was evaporated. The residue was dried, yielding 0.24 g (6%) of (±)-trans-4-[1-[3,5-bis(trifluoromethyl)benzoyl]-2-[(3,5-difluorophenyl)methyl]-4-piperidinyl]-N-(2,6-dimethylphenyl)-1-piperazineacetamide (compound 133).

EXAMPLE B.13

3,5 di(trifluormethyl)benzoyl chloride (0.0011 mol) was added to a mixture of (±)-trans-4-[2-[(3,4-dichlorophenyl)methyl]-4-piperidinyl]-N-(2,6-dimethylphenyl)-1-piperazineacetamide (0.001 mol) in DCM (20ml). The mixture was stirred for 5 minutes. Triethylamine (2ml) was added. The mixture was stirred at RT for 3 hours, washed with a diluted NaOH solution and with water, and then dried. The solvent was evaporated. The residue was purified by column chromatography over silica gel (eluent: $CH_2Cl_2$/$CH_3OH$ 96/4). The pure fractions were collected and the solvent was evaporated. The residue was crystallized from $CH_3CN$. The precipitate was filtered off and dried, yielding 0.32 g (44%) of (±)-trans-4-[1-[3,5-bis(trifluoromethyl)benzoyl]-2-[(3,4-dichlorophenyl)methyl]-4-piperidinyl]-N-(2,6-dimethylphenyl)-1-piperazineacetamide (compound 139).

EXAMPLE B.14

A mixture of compound 15 (0.01 mol) and imidazo[1,2-a]pyridin-2-carboxaldehyde (0.01 mol) in methanol (250 ml) was hydrogenated at RT overnight with palladium on activated carbon (10%, 2 g) as a catalyst in the presence of thiophene (4% solution, 2 ml). After uptake of hydrogen, the catalyst was filtered off and the filtrate was evaporated. The residue was purified over silica gel on a glass filter (eluent: $CH_2Cl_2/CH_3OH$ 100/0, 99/1, 98/2, 97/3 and 96/4). The pure fractions were collected and the solvent was evaporated. The residue was converted into the fumaric acid salt (1:2) from ethanol. The precipitate was filtered off and dried, yielding 2.8 g (32%) of (±)-cis-1-[3,5 -bis(trifluoromethyl)benzoyl]-4-[4-(imidazo[1,2-a]pyridin-2-ylmethyl)-1-piperazinyl]-2-(phenylmethyl)piperidine (E)-2-butenedioate(1:2) (compound 111).

EXAMPLE B.15

(±)-(B-trans)-4-[1-[3,5-bis(trifluoromethyl)benzoyl]-2-(phenylmethyl)-4-piperidinyl]-N-(2,6-dimethylphenyl)-1-piperazineacetamide (0.003 mol) was dissolved in ethanol (20 ml). A solution of fumaric acid (0.003 mol) in ethanol (15 ml) was added and the mixture was stood for 7 days. The precipitate was filtered off and dried, yielding 1.2 g of (B-trans)-4-[1-[3,5-bis(trifluoromethyl)benzoyl]-2-(phenylmethyl)-4-piperidinyl]-N-(2,6-dimethylphenyl)-1-piperazineacetamide (E)-2-butenedioate(1:1) (compound 128).

EXAMPLE B.16

A mixture of (±)-1-[3,5-bis(trifluoromethyl)benzoyl]-5-(phenylmethyl)-3-pyrrolidinone (0.0037 mol) and N-(2,6-dimethylphenyl)-1-piperazineacetamide (0.0037 mol) in methanol (150 ml) was hydrogenated at 50° C. with palladium on activated carbon (10%, 1 g) as a catalyst in the presence of tiophene solution (1 ml). After uptake of hydrogen, the catalyst was filtered off and the filtrate was evaporated. The residue was purified by column chromatography over silica gel (eluent: $CH_2Cl_2/CH_3OH$ 95/5). The desired fractions were collected and the solvent was evaporated. The residue was dried and then crystallized from DIPE. The precipitate was filtered off and dried, yielding 0.35 g (15%) of (±)-cis-4-[1-[3,5-bis(trifluoromethyl)benzoyl]-5-(phenylmethyl)-3-pyrrolidinyl]-N-(2,6-dimethylphenyl)-1-piperazineacetamide (compound 131).

EXAMPLE B.17

(±)-cis-1-(phenylmethyl)-4-[2-(phenylmethyl)-1-piperidinyl]piperazine (0.00043 mol) was added to 3,4-dichlorobenzeneacetic acid (+0.0004 mol) and 1-hydroxybenzotriazole hydrate (0.080 g) in DCM (5 ml). The mixture was stirred and cooled on an ice/ethanol-bath, under $N_2$ flow. Triethylamine was added dropwise. A solution of 1-(3-dimethylaminopropyl)-3-ethylcarbodiimide hydrochloride (0.120 g) in DCM (5 ml) was added and the reaction mixture was allowed to warm to RT, under $N_2$. The reaction mixture was stirred overnight. The mixture was diluted with $CH_2Cl_2$, until a 15-ml total volume was obtained. Then, the compound was isolated and purified by HPLC over silica gel (eluent: $CH_2Cl_2$ to $CH_2Cl_2/CH_3OH$ 90/10 over 20 minutes at 125 ml/minute). The desired fractions were collected and the solvent was evaporated, yielding 0.020 g of (±)-cis-1-[(3,4-dichlorophenyl)acetyl]-2-(phenylmethyl)-4-[4-(phenylmethyl)-1-piperazinyl]piperidine (compound 181).

EXAMPLE B.18

3,5-di(trifluoromethyl)-1-isocyanatobenzene (0.0025 mol) in DCM (10 ml) was added to a mixture of (±)-trans-N-(2,6-dimethylphenyl)-4-[2-(phenylmethyl)-4-piperidinyl]-1-piperazineacetamide (0.0025 mol) in DCM (15 ml). The mixture was stirred at RT overnight. The precipitate was filtered off and dried, yielding 0.66 g (40%) of (±)-trans-4-[1-[[[3,5-bis(trifluoromethyl)phenyl]amino]carbonyl]-2-(phenylmethyl)-4-piperidinyl]-N-(2,6-dimethylphenyl)-1-piperazineacetamide (compound 143).

EXAMPLE B.19

A mixture of (±)-1-[3,5-bis(trifluoromethyl)benzoyl]-2-[[3-fluoro-5-(trifluoromethyl)phenyl]methyl]-4-piperidinone (0.01 mol) and N-(2,6-dimethylphenyl)-1-piperazine-acetamide (0.01 mol) in 2-propanol (150 ml) was hydrogenated at 50C with platinum on activated carbon (5%; 2 g) as a catalyst in the presence of titanium(IV) isopropoxide (2.84 g) and thiophene solution (1 ml). After uptake of hyrogen, the catalyst was filtered off and the filtrate was evaporated. The residue was taken up in $CH_2Cl_2$ and $H_2O$. The organic layer was separated, washed several times with $H_2O$, dried, filtered over dicalite and the solvent was evaporated. This fraction was purified by HPLC over silica gel (eluent: $CH_2Cl_2/CH_3OH$ 98/2). Two pure fractions were collected and their solvents were evaporated. The residue was dried, yielding 0.72 g (10%) of (±)-cis-4-[1-[3,5-bis(trifluoromethyl)benzoyl]-2-[[3-fluoro-5-(trifluoromethyl)phenyl]methyl]-4-piperidinyl]-N-(2,6-dimethylphenyl)-1-piperazineacetamide (compound 140) and 0.88 g (12%) of (±)-trans-4-[1-[3,5-bis(trifluoromethyl)benzoyl]-2-[[3-fluoro-5-(trifluoro-methyl)phenyl]methyl]-4-piperidinyl]-N-(2,6-dimethylphenyl)-1-piperazineacetamide (compound 141).

Tables 1 to 4 list compounds of formula (I) that were prepared according to one or more of the foregoing examples (Ex.).

TABLE 1

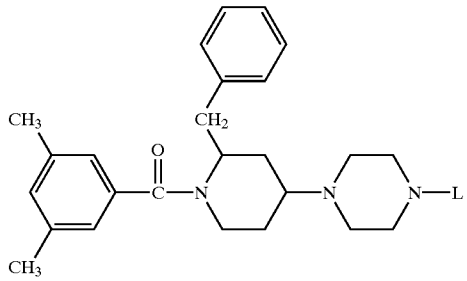

| Co. No. | Ex. | —L | Physical data (mp = melting point) |
|---|---|---|---|
| 1 | 6 | —H | (±)-cis |
| 2 | 6 | —H | (±)-trans |
| 3 | 9 | —CH₂—⌬ | (±)-cis; mp 196.9° C. |

TABLE 1-continued

[Structure: 3,5-dimethylbenzoyl-piperidine (with 2-benzyl substituent) connected to piperazine-L]

| Co. No. | Ex. | —L | Physical data (mp = melting point) |
|---|---|---|---|
| 4 | 9 | —CH₂—phenyl | (±)-trans |
| 5 | 5 | —CH₂—C(=O)—NH—(2,6-dimethylphenyl) | (±)-cis; mp 94.0° C. |
| 6 | 5 | —CH₂—C(=O)—NH—(2,6-dimethylphenyl) | (±)-trans |
| 7 | 8 | —CH₂—CH=CH—phenyl (E) | (±)-cis-(E); mp 201.0° C. |
| 8 | 8 | —CH₂—CH=CH—phenyl (E) | (±)-trans-(E); mp 210.1° C. |

TABLE 1-continued

[Structure: 3,5-dimethylbenzoyl-piperidine (with 2-benzyl substituent) connected to piperazine-L]

| Co. No. | Ex. | —L | Physical data (mp = melting point) |
|---|---|---|---|
| 9 | 8 | —C(=O)—(3,4,5-trimethoxyphenyl) | (±)-cis; mp 92.1° C. |
| 10 | 9 | 2-methoxyphenyl | (±)-cis; mp 72.8° C. |
| 11 | 9 | 2-methoxyphenyl | (±)-trans |
| 12 | 9 | —CH(phenyl)₂ | (±)-cis; mp 100.8° C. |
| 13 | 9 | —CH(phenyl)₂ | (±)-trans |

TABLE 2

| Co. No. | Ex. | n | p | —L | Physical data (mp = melting point) |
|---|---|---|---|---|---|
| 14 | B.2 | 1 | 1 | —H | (±)-trans |
| 15 | B.2 | 1 | 1 | —H | (±)-cis |
| 16 | B.1.a | 1 | 1 | —CH₂—C₆H₅ | (±)-cis; mp 143.8° C. |
| 17 | B.1.a + b | 1 | 1 | —CH₂—C₆H₅ | (±)-trans; mp 240.3° C.; fumaric acid (1:2) |
| 18 | B.1 | 1 | 1 | —CH₂—CH₂—(benzimidazol-2-one) | (±)-cis; mp 120° C. |
| 19 | B.1 | 1 | 1 | —CH₂—CH₂—(benzimidazol-2-one) | (±)-trans; mp 150° C. |
| 20 | B.1 | 1 | 1 | —C(O)-2-furyl | (±)-cis; mp 70.4° C. |
| 21 | B.1 | 1 | 1 | —C(O)-2-furyl | (±)-trans; mp 169.1° C. |
| 22 | B.1 | 1 | 1 | —CH₂—CH₂—O—CH₂—CH₃ on 2-methylbenzimidazole | (±)-trans; mp 173.8° C. |
| 23 | B.1 | 1 | 1 | —CH₂-(2-methyloxazol-5-yl)-CH₂-(2-methylbenzimidazole) | (±)-cis; mp 93.2° C. |

TABLE 2-continued

| Co. No. | Ex. | n | p | —L | Physical data (mp = melting point) |
|---|---|---|---|---|---|
| 24 | B.1 | 1 | 1 | CH₂-(2-methyl-oxazol-5-yl)-N-(2-methylbenzimidazol-1-yl) | (±)-trans; mp 100.1° C. |
| 25 | B.1 | 1 | 1 | -CH₂-(1-(2-ethoxyethyl)-imidazo[4,5-b]pyridin-2-yl) | (±)-trans; mp 75.4° C. |
| 26 | B.1 and B.3 | 1 | 1 | -CH₂-C(O)-NH-(2,6-dimethylphenyl) | (−)-(A)-trans; mp 97.4° C.; [α]$_D^{20}$ = −5.81° (c = 1% in DMF) |
| 27 | B.1 and B.3 | 1 | 1 | -CH₂-C(O)-NH-(2,6-dimethylphenyl) | (+)-(B)-trans; mp 96.8° C.; [α]$_D^{20}$ = +5.71° (c = 1% in DMF) |
| 28 | B.1 | 1 | 1 | cinnamyl | (±)-cis; (E) |
| 29 | B.1 | 1 | 1 | cinnamyl | (±)-trans; (E) |
| 30 | B.1 | 1 | 1 | 2-hydroxybenzyl | (±)-trans; mp 185.7° C. |
| 31 | B.1 | 1 | 1 | 2-hydroxybenzyl | (±)-cis; mp 77.5° C. |

TABLE 2-continued
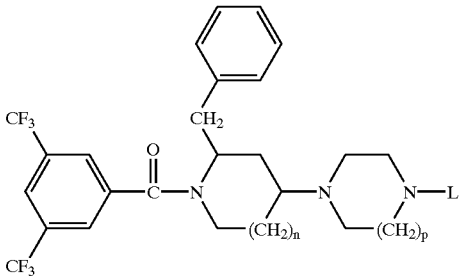
| Co. No. | Ex. | n | p | —L | Physical data (mp = melting point) |
|---|---|---|---|---|---|
| 32 | B.1 | 1 | 1 | 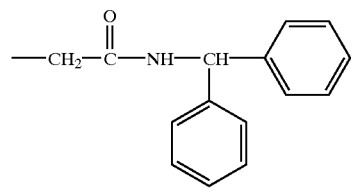 | (±)-cis; mp 183.1° C. |
| 33 | B.1 | 1 | 1 | 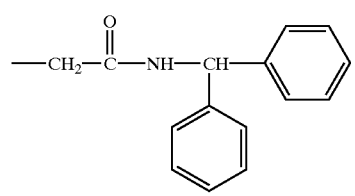 | (±)-trans; mp 115.6° C. |
| 34 | B.1 | 1 | 2 | 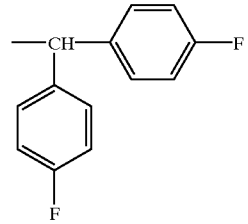 | (±)-trans; mp 120.1° C. |
| 35 | B.1 | 1 | 1 | 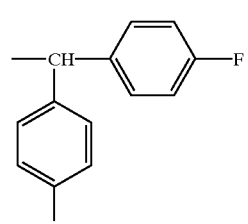 | (±)-cis; mp 150.9° C. |
| 36 | B.1 | 1 | 1 | 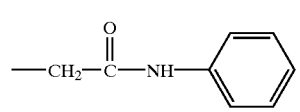 | (±)-trans; mp 120.8° C. |
| 37 | B.4 | 1 | 1 |  | (±)-cis; mp 85.6° C. |

TABLE 2-continued

[Structure: 3,5-bis(trifluoromethyl)benzoyl group attached to a piperidine ring bearing a benzyl (CH₂-phenyl) substituent, linked to a piperazine ring with N—L substituent; ring sizes indicated by (CH₂)ₙ and (CH₂)ₚ]

| Co. No. | Ex. | n | p | —L | Physical data (mp = melting point) |
|---|---|---|---|---|---|
| 38 | B.4 | 1 | 1 | —CH₂—C(=O)—NH—(2-methoxyphenyl) | (±)-trans; mp 170.5° C. |
| 39 | B.4 | 1 | 1 | —CH₂—CH₂—OH | (±)-cis; mp 192.9° C. |
| 40 | B.4 | 1 | 1 | 2-(1H-benzimidazolyl) | (±)-trans; mp 240.7° C. |
| 41 | B.4 | 1 | 1 | —CH₂—C(=O)—NH—(2,6-dimethylphenyl) | (+)-(A)-cis; mp 177.3° C.; $[\alpha]_D^{20} = +19.88°$ (c = 1% in methanol) |
| 42 | B.4 | 1 | 1 | —CH₂—C(=O)—NH—(2,6-dimethylphenyl) | (−)-(B)-cis; mp 177.3° C.; $[\alpha]_D^{20} = -20.34°$ (c = 1% in methanol) |
| 43 | B.4 | 1 | 1 | —CH(phenyl)—C(=O)—O—(3,5-dimethylphenyl) | (±)-cis; mp 88.1° C. |
| 44 | B.4 | 1 | 1 | —CH₂—CH₂—phenyl | (±)-cis; mp 227.1° C.; fumaric acid (1:2) |
| 45 | B.4 | 1 | 1 | —CH₂—C(=O)—NH—(2,6-dichlorophenyl) | (±)-trans; mp 200.2° C. |

TABLE 2-continued
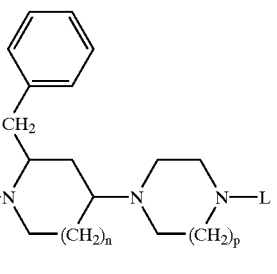
| Co. No. | Ex. | n | p | —L | Physical data (mp = melting point) |
|---|---|---|---|---|---|
| 46 | B.4 | 1 | 1 | 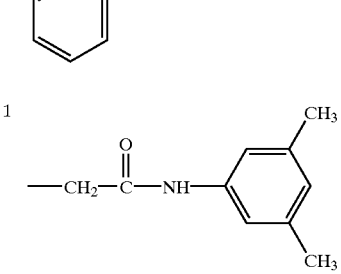 | (±)-trans; mp 105.6° C. |
| 47 | B.4 | 1 | 1 | 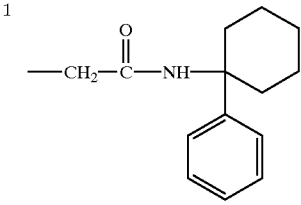 | (±)-cis; mp 89.2° C. |
| 48 | B.1 | 1 | 1 | 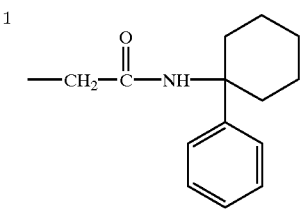 | (±)-trans; mp 89.7° C. |
| 49 | B.1 | 1 | 1 | 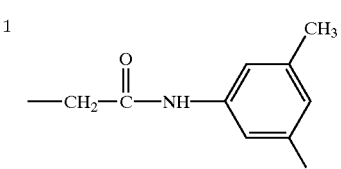 | (±)-cis; mp 135.8° C. |
| 50 | B.4 | 1 | 1 | 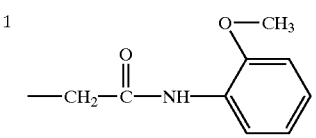 | (±)-trans; mp 140.4° C. |
| 51 | B.4 | 1 | 1 |  | (±)-cis; mp 173.5° C. |

TABLE 2-continued
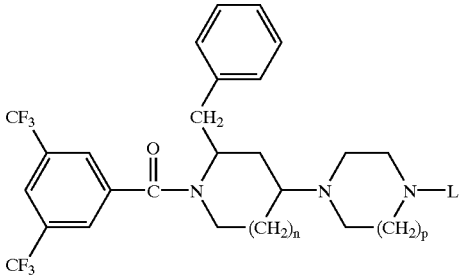
| Co. No. | Ex. | n | p | —L | Physical data (mp = melting point) |
|---|---|---|---|---|---|
| 52 | B.4 | 1 | 1 | 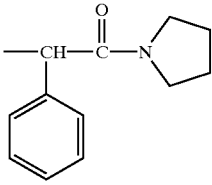 | (±)-cis; mp 101.5° C. |
| 53 | B.4 | 1 | 1 | 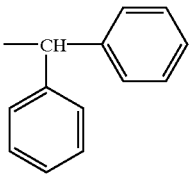 | (±)-trans; mp 185.8° C. |
| 54 | B.5 | 1 | 1 | 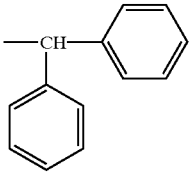 | (±)-cis; mp 260° C. |
| 55 | B.5 | 1 | 1 | 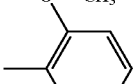 | (±)-trans; mp 75.2° C. |
| 56 | B.5 | 1 | 1 | 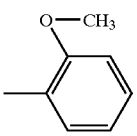 | (±)-trans; mp 80.1° C. |
| 57 | B.5 | 1 | 1 | 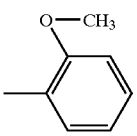 | (±)-cis |
| 58 | B.1 | 1 | 1 | 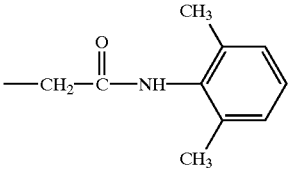 | (±) |

TABLE 2-continued
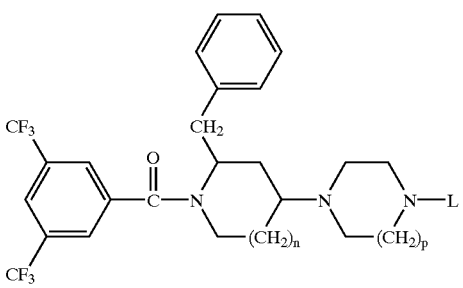
| Co. No. | Ex. | n | p | —L | Physical data (mp = melting point) |
|---|---|---|---|---|---|
| 59 | B.4 | 1 | 1 | 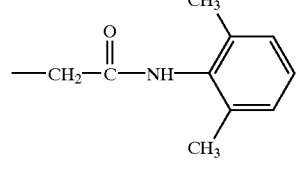 | (±)-cis; mp 106.4° C. |
| 60 | B.6 | 1 | 1 | —CH$_2$—CH(OH)—C$_6$H$_5$ | (±)-cis |
| 61 | B.6 | 1 | 1 | 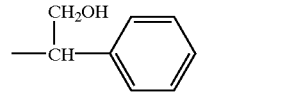 | (±)-cis |
| 62 | B.1 | 1 | 1 | 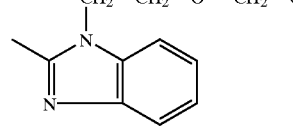 | (±)-cis |
| 63 | B.1 | 1 | 2 | —CH$_2$—C$_6$H$_5$ | (±)-cis; fumaric acid (1:2) |
| 64 | B.2 | 1 | 2 | —H | (±)-cis |
| 65 | B.4 | 1 | 2 | 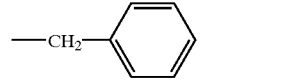 | (±)-cis |
| 66 | B.1 | 1 | 1 | 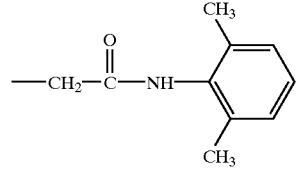 | (±)-cis |

TABLE 2-continued

| Co. No. | Ex. | n | p | —L | Physical data (mp = melting point) |
|---|---|---|---|---|---|
| 67 | B.1 | 1 | 1 | —(CH₂)₂—NH—[1-(4-fluorobenzyl)-1H-benzimidazol-2-yl] | (±)-trans |
| 68 | B.1 | 1 | 2 | —CH₂—C₆H₅ | (±)-trans; fumaric acid (1:2) |
| 69 | B.4 | 1 | 1 | —CH₂—C(=O)—NH—[1-(2-ethoxyethyl)-1H-benzimidazol-2-yl] | (±)-trans |
| 70 | B.7 | 1 | 1 | —CH₂—[1H-benzimidazol-1-yl, 2-methyl]; with CH₂-(2-methyloxazol-5-yl) substituent | (±)-cis |
| 71 | B.4 | 1 | 1 | —CH₂—C(=O)—NH—(3,5-bis(trifluoromethyl)phenyl) | (±)-cis |
| 72 | B.4 | 1 | 1 | —CH₂—C(=O)—NH—(2,6-bis(trifluoromethyl)-4-nitrophenyl) | (±)-cis |
| 73 | B.4 | 1 | 1 | —(CH₂)₂—C(=O)—NH—(2,6-dimethylphenyl) | (±)-cis; fumaric acid (1:2) |

TABLE 2-continued
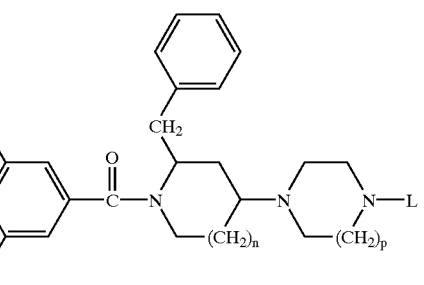
| Co. No. | Ex. | n | p | —L | Physical data (mp = melting point) |
|---|---|---|---|---|---|
| 74 | B.4 | 1 | 1 | 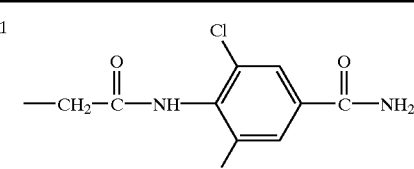 | (±)-cis |
| 75 | B.4 | 1 | 1 | 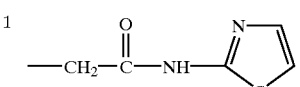 | (±)-cis; fumaric acid (1:1) |
| 76 | B.4 | 1 | 1 | —CH$_2$—C(=O)—NH—CH(CH$_3$)$_2$ | (±)-cis |
| 77 | B.2 | 1 | 2 | —H | (±)-trans |
| 78 | B.4 | 1 | 2 | 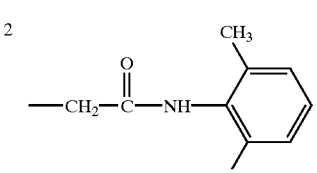 | (±)-trans |
| 79 | B.8 | 1 | 1 | 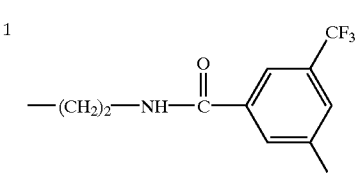 | (±)-cis |
| 80 | B.1 | 1 | 1 | 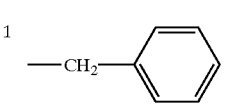 | (+)-(B)-trans |
| 81 | B.2 | 1 | 1 | —H | (+)-(B)-trans |
| 82 | B.1 | 1 | 1 | 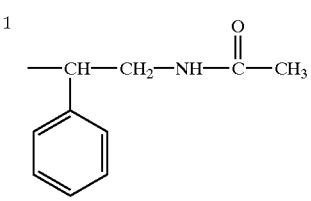 | (±)-cis |

TABLE 2-continued

[Structure: 3,5-bis(trifluoromethyl)benzoyl group attached to N of piperidine ring bearing a benzyl (CH₂-phenyl) substituent and linked via (CH₂)ₙ to a piperazine N-(CH₂)ₚ-L]

| Co. No. | Ex. | n | p | —L | Physical data (mp = melting point) |
|---|---|---|---|---|---|
| 83 | B.1 | 1 | 1 | —CH(phenyl)—CH₂—NH—C(=O)—CH₃ | (±)-trans |
| 84 | B.4 | 1 | 1 | —CH₂—C(=O)—NH—(1-methyl-1H-imidazol-2-yl) | (±)-cis |
| 85 | B.7 | 1 | 1 | —CH₂—(2-methylbenzimidazol-1-yl) linked to 2-methyloxazol-5-yl-methyl | (±)-trans |
| 86 | B.6 | 1 | 1 | —CH₂—CH(OH)—phenyl | (±)-trans |
| 87 | B.1 | 1 | 1 | —CH₂—CH(phenyl)—O—CH₂—(3,5-dimethylphenyl) | (±)-trans |
| 88 | B.1 | 1 | 1 | —CH₂—CH(phenyl)—O—CH₂—(3,5-dimethylphenyl) | (±)-cis; fumaric acid (1:2) |
| 89 | B.4 | 1 | 1 | —(CH₂)₂—OH | (±)-trans |
| 90 | B.11 | 1 | 1 | —(CH₂)₂—phenyl | (±)-trans; fumaric acid (1:2) |

TABLE 2-continued

[Structure: 3,5-bis(trifluoromethyl)benzoyl group attached to a piperidine ring bearing a benzyl (CH₂-phenyl) substituent and a -(CH₂)ₙ- linker to a piperazine ring with -(CH₂)ₚ-L substituent]

| Co. No. | Ex. | n | p | —L | Physical data (mp = melting point) |
|---|---|---|---|---|---|
| 91 | B.4 | 1 | 1 | —(CH₂)₃—C(=O)—NH—(2,6-dimethylphenyl) | (±)-trans; fumaric acid (1:2) |
| 92 | B.11 | 1 | 1 | —(CH₂)₂—CH(3,4-dichlorophenyl)—CH₂—N(CH₃)—C(=O)—phenyl | (±)-trans |
| 93 | B.11 | 1 | 1 | —(CH₂)₂—CH(3,4-dichlorophenyl)—CH₂—N(CH₃)—C(=O)—phenyl | (±)-cis; fumaric acid (1:2) |
| 94 | B.4 | 1 | 1 | —CH(phenyl)—C(=O)—NH—(2,6-dimethylphenyl) | (±)-trans |
| 95 |  | 1 | 1 | —CH₂—C(=O)—NH—(2,6-dimethylphenyl) | (B)-trans; (L)-malic acid (1:1) |
| 96 | B.4 | 1 | 1 | —(CH₂)₂—N(tetrazolinon-5-yl)—N—C₂H₅ | (±)-trans; fumaric acid (1:2) |

TABLE 2-continued
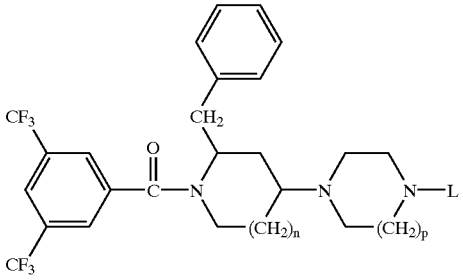
| Co. No. | Ex. | n | p | —L | Physical data (mp = melting point) |
|---|---|---|---|---|---|
| 97 | B.4 | 1 | 1 | 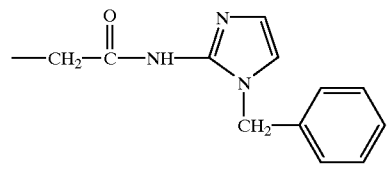 | (±)-trans |
| 98 | B.4 | 1 | 1 | 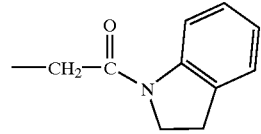 | (±)-cis |
| 99 | B.4 | 1 | 1 | 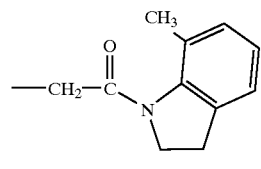 | (±)-cis |
| 100 | B.4 | 1 | 1 | 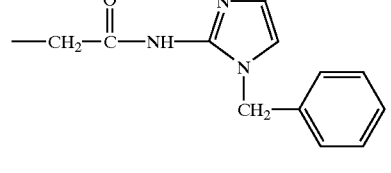 | (±)-cis |
| 101 | B.4 | 1 | 1 | 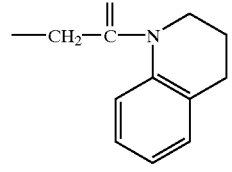 | (±)-cis |
| 102 | B.4 | 1 | 1 | 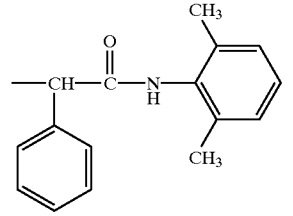 | (±)-cis |

TABLE 2-continued

Structure: 3,5-bis(trifluoromethyl)benzoyl-piperidine with benzyl substituent, connected via (CH₂)ₙ to piperazine-(CH₂)ₚ-L

| Co. No. | Ex. | n | p | —L | Physical data (mp = melting point) |
|---|---|---|---|---|---|
| 103 | B.4 | 1 | 1 | —(CH₂)₃—C(=O)—NH—(2,6-dimethylphenyl) | (±)-cis fumaric acid (1:2) |
| 104 | B.4 | 1 | 1 | —CH₂—C(=O)—(7-methyl-2,3-dihydroindol-1-yl) | (±)-trans |
| 105 | B.4 | 1 | 1 | —(CH₂)₂—C(=O)—NH—(2,6-dimethylphenyl) | (±)-trans |
| 106 | B.4 | 1 | 1 | —CH₂—C(=O)—NH—phenyl | (±)-trans |
| 107 | B.4 | 1 | 1 | —CH₂—C(=O)—(2,3-dihydroindol-1-yl) | (±)-trans |
| 108 | B.4 | 1 | 1 | —CH₂—C(=O)—NH—(3,5-bis(trifluoromethyl)phenyl) | (±)-trans |
| 109 | B.4 | 1 | 1 | —CH₂—C(=O)—NH—(1-methylimidazol-2-yl) | (±)-trans |
| 110 | B.14 | 1 | 1 | —CH₂—(imidazo[1,2-a]pyridin-2-yl) | (±)-trans; fumaric acid (1:2) |

TABLE 2-continued

[Structure: 3,5-bis(trifluoromethyl)benzoyl group on N of a piperidine bearing a benzyl (CH₂-phenyl) substituent and a (CH₂)ₙ linker to a piperazine N-(CH₂)ₚ-L]

| Co. No. | Ex. | n | p | —L | Physical data (mp = melting point) |
|---|---|---|---|---|---|
| 111 | B.14 | 1 | 1 | —CH₂—(imidazo[1,2-a]pyridin-2-yl) | (±)-cis; fumaric acid (1:2) |
| 112 | B.4 | 1 | 1 | —CH₂—C(=O)—NH—(thiazol-2-yl) | (±)-trans |
| 113 | B.1 | 1 | 1 | —CH₂—phenyl | (±)-trans |
| 114 | B.2 | 1 | 1 | H | (±)-trans; fumaric acid (1:2) |
| 115 | B.8 | 1 | 1 | —(CH₂)₂—NH—C(=O)—(3,5-dimethylphenyl) | (±)-trans |
| 116 | B.8 | 1 | 1 | —(CH₂)₂—NH—C(=O)—(3,5-dimethylphenyl) | (±)-cis |
| 117 | B.8 | 1 | 1 | —(CH₂)₂—NH—C(=O)—(3,5-bis(trifluoromethyl)phenyl) | (±)-trans |
| 118 | B.4 | 1 | 1 | —CH₂—C(=O)—(3,4-dihydroquinolin-1(2H)-yl) | (±)-trans; fumaric acid (1:2) |
| 119 | B.4 | 1 | 1 | —CH₂—(2-methyl-1,3-oxazol-5-yl) | (±)-trans |

TABLE 2-continued
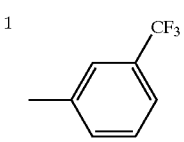
| Co. No. | Ex. | n | p | —L | Physical data (mp = melting point) |
|---|---|---|---|---|---|
| 120 | B.13 | 1 | 1 | 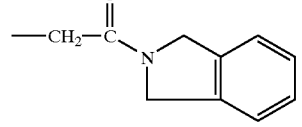 | (±)-trans |
| 121 | B.1 | 1 | 1 | 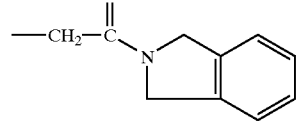 | (±)-cis |
| 122 | B.1 | 1 | 1 | 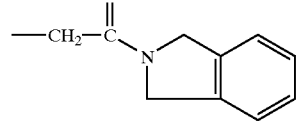 | (±)-trans |
| 123 | B.4 | 1 | 1 | 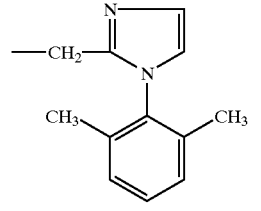 | (±)-cis |
| 124 | B.15 | 1 | 1 | 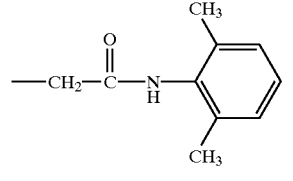 | (B)-trans; benzoate (1:1) |
| 125 | B.15 | 1 | 1 | 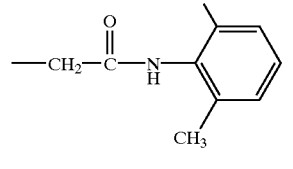 | (B)-trans; maleic acid (1:1) |

TABLE 2-continued
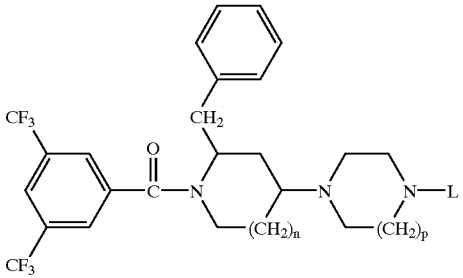
| Co. No. | Ex. | n | p | —L | Physical data (mp = melting point) |
|---|---|---|---|---|---|
| 126 | B.15 | 1 | 1 | 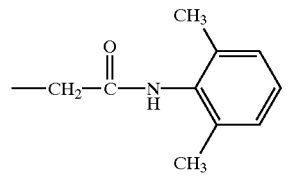 | (B)-trans; hydrochloric acid (1:2) hydrate (1:1) |
| 127 | B.15 | 1 | 1 | 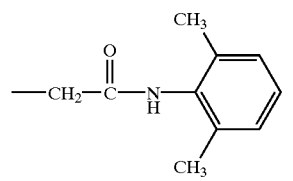 | (B)-trans; succinic acid (1:1) |
| 128 | B.15 | 1 | 1 | 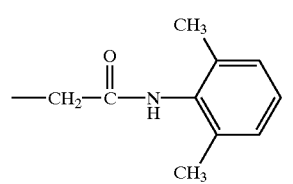 | (B)-trans; fumaric acid (1:1) |
| 129 | B.9 | 1 | 1 | 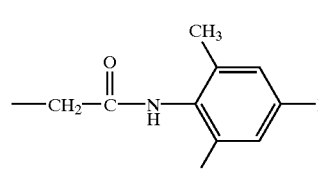 | (±)-cis; fumaric acid (1:2) |
| 130 | B.10 | 1 | 1 | —CH$_3$ | (±)-cis; fumaric acid (1:2) |
| 131 | B.16 | 0 | 1 | 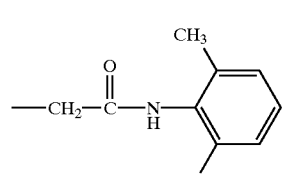 | (±)-cis |

TABLE 3

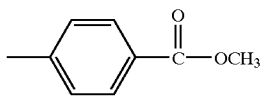

| Co. No. | Ex. | X& | R² | Rₐ | R_b | R_c | Physical data |
|---|---|---|---|---|---|---|---|
| 132 | B.12 | c.b. | 3,5-di(trifluoro-methyl)phenyl | F | H | F | (±)-cis |
| 133 | B.12 | c.b. | 3,5-di(trifluoro-methyl)phenyl | F | H | F | (±)-trans |
| 134 | B.12 | c.b. | 3,5-di(trifluoro-methyl)phenyl | H | F | F | (±)-cis |
| 135 | B.12 | c.b. | 3,5-di(trifluoro-methyl)phenyl | H | F | F | (±)-trans |
| 136 | B.4 | c.b. | 3,5-di(trifluoro-methyl)phenyl | H | CF₃ | H | (±)-(B) fumaric acid (1:1) |
| 137 | B.4 | c.b. | 3,5-di(trifluoro-methyl)phenyl | H | CF₃ | H | (±)-(A) |
| 138 | B.13 | c.b. | 3,5-di(trifluoro-methyl)phenyl | H | Cl | Cl | (±)-cis |
| 139 | B.13 | c.b. | 3,5-di(trifluoro-methyl)phenyl | H | Cl | Cl | (±)-trans |
| 140 | B.19 | c.b. | 3,5-di(trifluoro-methyl)phenyl | F | H | CF₃ | (±)-cis |
| 141 | B.19 | c.b. | 3,5-di(trifluoro-methyl)phenyl | F | H | CF₃ | (±)-trans |
| 142 | B.13 | c.b. | 3-isopropoxyphenyl | H | H | H | (±)-cis |
| 143 | B.18 | —NH— | 3,5-di(trifluoro-methyl)phenyl | H | H | H | (±)-trans |
| 144 | B.13 | c.b. | phenyl | H | H | H | (±)-cis |
| 145 | B.13 | c.b. | 2-naphtyl | H | H | H | (±)-trans |
| 146 | B.13 | c.b. | 2-quinolinyl | H | H | H | (±)-trans |
| 147 | B.13 | c.b. | 2-quinoxalinyl | H | H | H | (±)-trans |
| 148 | B.13 | —O— | benzyl | H | H | H | (±)-trans |
| 149 | B.17 | c.b. | 3-methyl-benzofuran-2-yl | H | H | H | (±)-trans |
| 150 | B.17 | c.b. | 5-fluoro-indol-2-yl | H | H | H | (±)-trans |
| 151 | B.17 | c.b. | 5-indolyl | H | H | H | (±)-trans |
| 152 | B.17 | c.b. | 5-methyl-pyrazin-2-yl | H | H | H | (±)-trans |
| 153 | B.13 | c.b. | phenyl | H | H | H | (±)-trans |
| 154 | B.13 | c.b. | 5-methyl-isoxazol-3-yl | H | H | H | (±)-trans |
| 155 | B.13 | c.b. | 2,4,6-trimethylphenyl | H | H | H | (±)-cis |
| 156 | B.13 | c.b. | 3,4,5-trimethoxyphenyl | H | H | H | (±)-cis |
| 157 | B.13 | c.b. | 3-cyanophenyl | H | H | H | (±)-cis |
| 158 | B.13 | c.b. | 4-(C(O)OCH₃)phenyl | H | H | H | (±)-cis |
| 159 | B.13 | c.b. | 3,5-difluorophenyl | H | H | H | (±)-cis |
| 160 | B.13 | c.b. | 2,6-dichloro-pyridin-4-yl | H | H | H | (±)-cis |
| 161 | B.13 | c.b. | 2-naphtyl | H | H | H | (±)-cis |
| 162 | B.13 | c.b. | 2-quinolinyl | H | H | H | (±)-cis |
| 163 | B.13 | c.b. | 3-isopropoxybenzyl | H | H | H | (±)-cis |
| 164 | B.13 | c.b. | 1-phenylethyl | H | H | H | (±)-cis |
| 165 | B.13 | c.b. | 3-isopropoxyphenyl | H | H | H | (±)-trans |
| 166 | B.13 | c.b. | 3-cyanophenyl | H | H | H | (±)-trans |

TABLE 3-continued

[Structure: benzyl-substituted piperidine-piperazine with 2,6-dimethylanilide acetamide, Ra, Rb, Rc on phenyl; R²–X–C(=O)–N(piperidine)]

| Co. No. | Ex. | X[&] | R² | Ra | Rb | Rc | Physical data |
|---|---|---|---|---|---|---|---|
| 167 | B.13 | c.b. | 4-(C(=O)OCH₃)-phenyl | H | H | H | (±)-trans |
| 168 | B.13 | c.b. | 2,4-dichlorophenyl | H | H | H | (±)-trans |
| 169 | B.13 | c.b. | 2-thienyl | H | H | H | (±)-trans |

[&] c.b. = covalent bond

TABLE 4

[Structure: 4-Ra-benzyl piperidine linked to piperazine-L; R²–X–C(=O)–N(piperidine)]

| Co. No. | Ex. | Ra | X[&] | R² | L | Physical data |
|---|---|---|---|---|---|---|
| 170 | B.1 | CF₃ | c.b. | 3,5-di(trifluoro-methyl)phenyl | H | (±)-(A) |
| 171 | B.1 | CF₃ | c.b. | 3,5-di(trifluoro-methyl)phenyl | H | (±)-(B) fumaric acid (1:4) |
| 172 | B.13 | H | c.b. | 3-trifluoromethyl-phenyl | benzyl | (±)-cis |
| 173 | B.13 | H | c.b. | 3,5-difluoro-phenyl | benzyl | (±)-cis |
| 174 | B.13 | H | c.b. | 2-naphtyl | benzyl | (±)-cis |
| 175 | B.13 | H | c.b. | 3-cyano-phenyl | benzyl | (±)-cis |
| 176 | B.13 | H | —O— | benzyl | benzyl | (±)-cis |
| 177 | B.13 | H | c.b. | 2-furanyl | benzyl | (±)-cis |
| 178 | B.13 | H | c.b. | 2-thienyl | benzyl | (±)-cis |
| 179 | B.13 | H | c.b. | phenyl | benzyl | (±)-cis |
| 180 | B.13 | H | c.b. | 3,5-dichloro-phenyl | benzyl | (±)-cis |
| 181 | B.17 | H | c.b. | 3,4-dichlorophenyl | benzyl | (±)-cis |
| 182 | B.13 | H | c.b. | 4-(C(=O)OCH₃)-phenyl | benzyl | (±)-cis |
| 183 | B.13 | H | c.b. | phenyl | benzyl | (±)-trans |
| 184 | B.13 | H | c.b. | 2,6-dichloro-pyridin-4-yl | benzyl | (±)-trans |
| 185 | B.13 | H | c.b. | 2-furanyl | benzyl | (±)-trans |
| 186 | B.13 | H | c.b. | 2-thienyl | benzyl | (±)-trans |
| 187 | B.13 | H | c.b. | 3-cyano-phenyl | benzyl | (±)-trans |
| 188 | B.13 | H | c.b. | 4-(C(=O)OCH₃)-phenyl | benzyl | (±)-trans |

TABLE 4-continued

[Structure: piperidine-piperazine compound with R_a-phenyl-CH2 substituent, R²-X-C(=O)-N linkage and N-L group]

| Co. No. | Ex. | R_a | X[&] | R² | L | Physical data |
|---|---|---|---|---|---|---|
| 189 | B.13 | H | c.b. | benzothiophen-2-yl | benzyl | (±)-trans |
| 190 | B.13 | H | c.b. | 5-methyl-isoxazol-3-yl | benzyl | (±)-trans |
| 191 | B.13 | H | c.b. | 2-nitrophenyl | benzyl | (±)-cis |
| 192 | B.16 | H | c.b. | 2-aminophenyl | benzyl | (±)-cis fumaric acid (1:2) |

[&] c.b. = covalent bond

Table 5 lists both the experimental (column heading "Exp") and theoretical (column heading "Theor") elemental analysis values for carbon, hydrogen and nitrogen for the compounds as prepared in the experimental part hereinabove.

TABLE 5

| Co. No. | C Exp | C Theor | H Exp | H Theor | N Exp | N Theor |
|---|---|---|---|---|---|---|
| 5 | 75.47 | 76.05 | 8.06 | 8.02 | 9.91 | 10.14 |
| 6 | 75.08 | 76.05 | 8.18 | 8.02 | 10.02 | 10.14 |
| 7 | 68.40 | 68.18 | 6.68 | 6.68 | 5.52 | 5.68 |
| 8 | 67.39 | 68.18 | 6.83 | 6.68 | 5.62 | 5.68 |
| 9 | 71.98 | 71.77 | 7.59 | 7.40 | 7.11 | 7.17 |
| 10 | 76.99 | 77.23 | 8.12 | 7.90 | 8.16 | 8.44 |
| 12 | 81.31 | 81.83 | 7.79 | 7.77 | 7.36 | 7.53 |
| 16 | 64.88 | 65.19 | 5.53 | 5.64 | 7.05 | 7.13 |
| 17 | 58.45 | 58.46 | 4.85 | 5.03 | 5.01 | 5.11 |
| 19 | 61.61 | 61.91 | 5.03 | 5.35 | 10.32 | 10.62 |
| 20 | 60.51 | 60.71 | 4.92 | 4.92 | 6.89 | 7.08 |
| 21 | 60.74 | 60.71 | 4.86 | 4.92 | 7.02 | 7.08 |
| 22 | 63.09 | 62.87 | 5.56 | 5.72 | 10.08 | 10.18 |
| 23 | 62.68 | 62.98 | 5.21 | 5.28 | 1.43 | 11.60 |
| 24 | 62.44 | 62.98 | 5.18 | 5.28 | 11.33 | 11.60 |
| 25 | 60.33 | 61.53 | 5.42 | 5.74 | 11.62 | 11.96 |
| 26 | 63.42 | 63.63 | 5.96 | 5.80 | 8.52 | 8.48 |
| 27 | 63.41 | 63.63 | 5.82 | 5.80 | 8.04 | 8.48 |
| 30 | 63.02 | 62.94 | 5.19 | 5.28 | 7.01 | 7.10 |
| 31 | 62.68 | 62.94 | 5.31 | 5.28 | 7.08 | 7.10 |
| 32 | 66.40 | 66.47 | 5.44 | 5.58 | 7.66 | 7.75 |
| 33 | 66.42 | 66.47 | 5.60 | 5.58 | 7.55 | 7.75 |
| 34 | 62.07 | 62.98 | 5.10 | 5.28 | 11.46 | 11.60 |
| 35 | 65.11 | 65.04 | 5.08 | 5.03 | 5.89 | 5.99 |
| 36 | 64.94 | 65.04 | 4.97 | 5.03 | 6.03 | 5.99 |
| 37 | 62.58 | 62.65 | 5.26 | 5.42 | 8.63 | 8.86 |
| 38 | 60.87 | 61.62 | 5.22 | 5.48 | 8.23 | 8.45 |
| 40 | 62.28 | 62.43 | 4.78 | 5.08 | 11.28 | 11.38 |
| 41 | 63.44 | 63.63 | 5.69 | 5.80 | 8.36 | 8.48 |
| 42 | 63.83 | 63.63 | 5.77 | 5.80 | 8.40 | 8.48 |
| 43 | 66.54 | 66.75 | 5.52 | 5.60 | 5.61 | 5.70 |
| 45 | 56.47 | 56.50 | 4.40 | 4.60 | 7.89 | 7.99 |
| 46 | 64.49 | 64.71 | 5.77 | 5.87 | 7.92 | 8.16 |
| 47 | 63.46 | 63.63 | 5.84 | 5.80 | 8.39 | 8.48 |
| 48 | 65.16 | 65.53 | 6.38 | 6.20 | 7.71 | 7.84 |
| 49 | 65.43 | 65.53 | 6.25 | 6.20 | 7.81 | 7.84 |
| 50 | 63.71 | 63.63 | 5.64 | 5.80 | 8.40 | 8.48 |
| 51 | 61.79 | 61.62 | 5.46 | 5.48 | 8.31 | 8.45 |
| 52 | 64.50 | 64.71 | 5.70 | 5.87 | 7.92 | 8.16 |
| 53 | 63.77 | 63.63 | 5.90 | 5.80 | 8.25 | 8.48 |
| 54 | 63.54 | 64.53 | 5.15 | 5.29 | 5.19 | 5.37 |
| 55 | 67.97 | 68.56 | 5.65 | 5.60 | 6.02 | 6.31 |
| 56 | 63.34 | 63.46 | 5.39 | 5.49 | 6.79 | 6.94 |
| 57 | 63.54 | 63.46 | 5.43 | 5.49 | 6.97 | 6.94 |
| 59 | 63.58 | 63.63 | 5.75 | 5.80 | 8.37 | 8.48 |
| 60 | 64.13 | 63.97 | 5.61 | 5.69 | 6.60 | 6.78 |
| 61 | 63.41 | 63.97 | 5.65 | 5.69 | 6.60 | 6.78 |
| 62 | 62.65 | 62.87 | 5.76 | 5.72 | 9.97 | 10.18 |
| 63 | 58.77 | 58.92 | 5.14 | 5.19 | 4.99 | 5.03 |
| 65 | 63.78 | 64.08 | 6.24 | 5.98 | 7.97 | 8.30 |
| 66 | 62.89 | 64.22 | 5.41 | 5.39 | 11.03 | 10.96 |
| 67 | 63.06 | 64.22 | 5.18 | 5.39 | 10.62 | 10.96 |
| 69 | 60.74 | 61.28 | 5.57 | 5.68 | 11.15 | 11.28 |
| 70 | 62.34 | 62.53 | 4.81 | 5.11 | 11.62 | 11.82 |
| 71 | 54.59 | 54.69 | 4.03 | 4.20 | 7.04 | 7.29 |
| 72 | 59.45 | 59.57 | 5.01 | 5.28 | 9.71 | 9.92 |
| 74 | 54.84 | 54.85 | 4.18 | 4.47 | 9.28 | 9.41 |
| 76 | 59.66 | 60.19 | 6.21 | 6.06 | 8.93 | 9.36 |
| 78 | 63.95 | 64.08 | 5.90 | 5.98 | 8.23 | 8.30 |
| 79 | 55.18 | 55.25 | 4.08 | 4.38 | 7.04 | 7.16 |
| 82 | 62.65 | 63.63 | 5.80 | 5.80 | 8.22 | 8.48 |
| 83 | 61.84 | 63.63 | 5.91 | 5.80 | 8.00 | 8.48 |
| 84 | 58.20 | 58.49 | 5.21 | 5.38 | 12.81 | 13.20 |
| 85 | 61.55 | 62.53 | 5.15 | 5.11 | 11.53 | 11.82 |
| 86 | 63.82 | 63.97 | 5.58 | 5.69 | 6.73 | 6.78 |
| 87 | 67.38 | 68.37 | 5.48 | 6.15 | 5.48 | 5.70 |
| 92 | 61.87 | 61.95 | 5.17 | 5.32 | 6.32 | 6.72 |
| 93 | 57.14 | 57.47 | 4.71 | 4.92 | 5.02 | 5.26 |
| 94 | 66.62 | 66.84 | 5.55 | 5.75 | 7.23 | 7.60 |
| 95 | 58.94 | 58.94 | 5.60 | 5.58 | 6.97 | 7.05 |
| 96 | 52.25 | 52.35 | 4.82 | 4.97 | 11.15 | 11.25 |
| 97 | 62.54 | 62.35 | 5.26 | 5.37 | 11.64 | 11.79 |
| 98 | 63.86 | 63.82 | 5.30 | 5.51 | 8.39 | 8.51 |
| 99 | 64.29 | 64.28 | 5.40 | 5.69 | 8.17 | 8.33 |
| 100 | 62.13 | 62.35 | 5.16 | 5.37 | 11.59 | 11.79 |
| 101 | 64.49 | 64.28 | 5.68 | 5.69 | 8.08 | 8.33 |
| 102 | 67.17 | 66.84 | 5.82 | 5.75 | 7.36 | 7.60 |

TABLE 5-continued

| Co. No. | C Exp | C Theor | H Exp | H Theor | N Exp | N Theor |
|---|---|---|---|---|---|---|
| 103 | 58.42 | 58.69 | 5.39 | 5.47 | 6.15 | 6.08 |
| 104 | 64.16 | 64.28 | 5.73 | 5.69 | 8.31 | 8.33 |
| 105 | 63.95 | 64.08 | 6.01 | 5.98 | 8.25 | 8.30 |
| 106 | 62.27 | 62.65 | 5.37 | 5.42 | 8.84 | 8.86 |
| 107 | 63.76 | 63.82 | 5.54 | 5.51 | 8.45 | 8.51 |
| 108 | 54.46 | 54.69 | 4.08 | 4.20 | 7.20 | 7.29 |
| 109 | 58.46 | 58.49 | 5.19 | 5.38 | 12.90 | 13.20 |
| 110 | 56.57 | 57.14 | 4.58 | 4.80 | 7.96 | 8.13 |
| 111 | 56.80 | 57.14 | 4.59 | 4.80 | 7.99 | 8.13 |
| 112 | 56.42 | 56.33 | 4.73 | 4.88 | 10.77 | 10.95 |
| 114 | 54.52 | 54.17 | 4.61 | 4.82 | 5.75 | 5.74 |
| 115 | 64.06 | 64.08 | 6.07 | 5.98 | 8.16 | 8.30 |
| 116 | 63.87 | 64.08 | 5.89 | 5.98 | 8.11 | 8.30 |
| 117 | 55.13 | 55.25 | 4.18 | 4.38 | 7.05 | 7.16 |
| 118 | 57.96 | 58.41 | 4.90 | 5.12 | 6.06 | 6.19 |
| 119 | 60.60 | 60.60 | 5.45 | 5.42 | 9.12 | 9.42 |
| 120 | 59.92 | 59.72 | 4.73 | 4.70 | 6.20 | 6.53 |
| 121 | 63.51 | 63.82 | 5.60 | 5.51 | 8.43 | 8.51 |
| 122 | 63.53 | 63.82 | 5.77 | 5.51 | 9.05 | 8.51 |
| 123 | 64.81 | 65.00 | 5.75 | 5.75 | 10.17 | 10.24 |
| 131 | 63.23 | 63.15 | 5.72 | 5.61 | 8.51 | 8.66 |
| 132 | 60.00 | 60.34 | 4.90 | 5.21 | 7.76 | 8.04 |
| 133 | 59.93 | 60.34 | 5.17 | 5.21 | 7.94 | 8.04 |
| 134 | 60.22 | 60.34 | 5.22 | 5.21 | 7.94 | 8.04 |
| 135 | 60.87 | 60.34 | 5.44 | 5.21 | 7.97 | 8.04 |
| 137 | 59.04 | 59.34 | 5.01 | 5.12 | 7.43 | 7.69 |
| 138 | 57.81 | 57.62 | 4.76 | 4.97 | 7.54 | 7.68 |
| 139 | 57.28 | 57.62 | 4.73 | 4.97 | 7.25 | 7.68 |
| 140 | 57.53 | 57.91 | 4.88 | 4.86 | 7.18 | 7.50 |
| 141 | 57.45 | 57.91 | 4.79 | 4.86 | 7.21 | 7.50 |
| 142 | 73.32 | 74.19 | 8.25 | 7.96 | 9.28 | 9.61 |
| 143 | 61.66 | 62.21 | 5.77 | 5.82 | 0.21 | 10.36 |
| 144 | 75.31 | 75.54 | 7.76 | 7.68 | 10.28 | 10.68 |
| 145 | 76.49 | 77.32 | 7.43 | 7.37 | 9.33 | 9.75 |
| 170 | 53.73 | 55.03 | 4.46 | 4.62 | 7.14 | 7.40 |
| 192 | 64.48 | 65.13 | 6.20 | 6.33 | 7.84 | 7.99 |

C. PHARMACOLOGICAL EXAMPLE

EXAMPLE C.1

Antagonism of Substance-P Induced Relaxation of the Pig Coronary Arteries

Segments of coronary arteries taken from pigs (killed by injection of an overdose of sodium pentobarbital) were inverted and mounted for recording of isometric tension in organ baths (volume 20 ml) with the endothelium at the outside. The preparations were bathed in Krebs-Henseleit solution. The solution was kept at 37° C. and gassed with a mixture of $O_2/CO_2$ (95/5). After stabilisation of the preparations, prostaglandin $F_{2\alpha}$ ($10^{-5}$ M) was administered to induce a contraction. This was repeated until contractile responses became stable. Then prostaglandin $F_{2\alpha}$ was again administered and substance P ($3\times10^{-10}$ M and $10^{-9}$ M cumulatively) was added. Substance P induced endothelium dependent relaxations. After washing away the agonists, a known concentration of a compound of formula (I) was added. After an incubation period of 30 minutes, prostaglandin $F_{2\alpha}$ ($10^{-5}$ M) and the same concentrations of substance P as described above were again administered in the presence of the compound to be tested. Relaxations caused by substance P were expressed as relaxations under control conditions, and percent inhibition of the response to $10^{-9}$ M substance P was taken as a measure of the antagonistic activity of the compound to be tested. Table 6 lists the $IC_{50}$ values (concentration at which 50% of the response to $10^{-9}$ M substance P was inhibited by the test compound) for the tested compounds.

TABLE 6

| Co. No. | $IC_{50}$ (in $10^{-9}$ M) | Co. No. | $IC_{50}$ (in $10^{-9}$ M) | Co. No. | $IC_{50}$ (in $10^{-9}$ M) |
|---|---|---|---|---|---|
| 5 | 4.61 | 51 | 1.35 | 97 | 1.58 |
| 17 | 1.68 | 52 | 1.10 | 99 | 1.46 |
| 19 | 0.54 | 53 | 0.35 | 101 | 0.75 |
| 22 | 0.37 | 55 | 2.8 | 102 | 1.85 |
| 24 | 0.64 | 56 | 3.25 | 104 | 0.30 |
| 25 | 0.79 | 58 | 0.24 | 105 | 1.05 |
| 26 | 2.75 | 59 | 1.20 | 107 | 0.96 |
| 27 | 0.13 | 61 | 15.2 | 105 | 2.23 |
| 28 | 13.3 | 62 | 0.24 | 119 | 2.81 |
| 29 | 0.45 | 63 | 8.38 | 120 | 0.82 |
| 33 | 0.60 | 65 | 6.39 | 121 | 2.77 |
| 34 | 0.35 | 68 | 5.88 | 122 | 1.68 |
| 35 | 17.0 | 69 | 1.57 | 124 | 0.06 |
| 36 | 2.31 | 70 | 0.29 | 128 | 0.35 |
| 37 | 9.60 | 73 | 5.73 | 132 | 2.08 |
| 38 | 0.86 | 76 | 14.1 | 133 | 0.62 |
| 42 | 0.93 | 85 | 0.15 | 134 | 0.04 |
| 43 | 5.63 | 86 | 2.13 | 135 | 0.01 |
| 44 | 8.34 | 87 | 1.90 | 136 | 0.31 |
| 45 | 0.15 | 91 | 0.07 | 137 | 0.23 |
| 46 | 0.42 | 92 | 0.78 | 138 | 0.16 |
| 48 | 0.26 | 93 | 4.99 | 139 | 0.13 |
| 49 | 0.59 | 94 | 0.42 | | |
| 50 | 2.43 | 95 | 0.10 | | |

EXAMPLE C.2

Antagonism of Substance P Induced Plasma Extravasation in Guinea-pigs

Plasma extravasation was induced by injection of substance P (2 mg/kg) in the femoral artery of female guinea-pigs. Evans Blue dye (30 mg/kg) was injected simultaneously. The test compound or solvent was administered 1 hour prior to substance P injection. 10 minutes after challenge, the animals were checked for blue colouring (a direct measure for plasma extravasation) of the nose, the forepaws, and the conjunctiva. 30 minutes after challenge, the animals were sacrificed by $CO_2$ gas inhalation and checked for blue colouring of the trachea and the urinary bladder. Doses which actively inhibit substance P-induced plasma extravasation are defined as thoses doses at which only ⅓ or less of the total surface area of the nose, forepaws, conjunctiva, trachea or urinary bladder are coloured blue by an intensive extravasation. Table 7 lists the lowest active doses LAD) in mg/kg for the tested compounds.

TABLE 7

| | LAD (in mg/kg) | | | | |
|---|---|---|---|---|---|
| Co. No. | nose | forepaws | conjunctiva | trachea | urinary bladder |
| 8 | 10.0 | 10.0 | 100 | >40.0 | >40.0 |
| 12 | >40.0 | >40.0 | >40.0 | >40.0 | 40.0 |
| 16 | 40.0 | 40.0 | 40.0 | >40.0 | >40.0 |
| 17 | 10.0 | 10.0 | 10.0 | >40.0 | 10.0 |
| 19 | 2.50 | 2.50 | 2.50 | 10.0 | >40.0 |
| 21 | 10.0 | 10.0 | 10.0 | >40.0 | 10.0 |
| 22 | 2.50 | 2.50 | 2.50 | 10.0 | >40.0 |
| 23 | 10.0 | 10.0 | >40.0 | >40.0 | >40.0 |
| 24 | 2.50 | 2.50 | 10.0 | 10.0 | >40.0 |
| 25 | 2.50 | 2.50 | 10.0 | >40.0 | >40.0 |
| 26 | 10.0 | 10.0 | 20.0 | 40.0 | 20.0 |
| 27 | 0.63 | 0.63 | 0.63 | 0.63 | 0.63 |
| 33 | 2.50 | 10.0 | 2.50 | >40.0 | >40.0 |

TABLE 7-continued

LAD (in mg/kg)

| Co. No. | nose | forepaws | conjunctiva | trachea | urinary bladder |
|---|---|---|---|---|---|
| 34 | 2.50 | 10.0 | 2.50 | 10.0 | 10.0 |
| 38 | 10.0 | 10.0 | 10.0 | >40.0 | >40.0 |
| 40 | 10.0 | 10.0 | 10.0 | >40.0 | >40.0 |
| 42 | 1.25 | 1.25 | 2.50 | 5.00 | 5.00 |
| 45 | 0.63 | 0.63 | 0.63 | >40.0 | 2.50 |
| 46 | 0.63 | 0.63 | 0.63 | >40.0 | 0.63 |
| 47 | 40.0 | 40.0 | 40.0 | >40.0 | >40.0 |
| 48 | 2.50 | 2.50 | 2.50 | 2.50 | 2.50 |
| 49 | 2.50 | 2.50 | 2.50 | 10.0 | >40.0 |
| 50 | 10.0 | 10.0 | 10.0 | 10.0 | >40.0 |
| 52 | 0.63 | 0.63 | 2.50 | 10.0 | 0.0 |
| 53 | 1.25 | 1.25 | 1.25 | 2.50 | 2.50 |
| 56 | 10.0 | 10.0 | 10.0 | 40.0 | 2.50 |
| 59 | 2.50 | 2.50 | 2.50 | 5.00 | 5.00 |
| 68 | 10.0 | 10.0 | >40.0 | >40.0 | >40.0 |
| 70 | 10.0 | 10.0 | 10.0 | 10.0 | 10.0 |
| 73 | 10.0 | 10.0 | 10.0 | >40.0 | >40.0 |
| 74 | 10.0 | 10.0 | 10.0 | >40.0 | >40.0 |
| 82 | 2.50 | 2.50 | 2.50 | 10.0 | >40.0 |
| 83 | 0.63 | 0.63 | 2.50 | >40.0 | 0.63 |
| 85 | 2.50 | 2.50 | 2.50 | 2.50 | 10.0 |
| 87 | 10.0 | 10.0 | 10.0 | 10.0 | >40.0 |
| 90 | 10.0 | 10.0 | 10.0 | 10.0 | >40.0 |
| 94 | 2.50 | 2.50 | 2.50 | 10.0 | 10.0 |
| 95 | 0.31 | 0.31 | 0.31 | 0.63 | 2.50 |
| 96 | 10.0 | 10.0 | 10.0 | >40.0 | >40.0 |
| 101 | 10.0 | 10.0 | 10.0 | >40.0 | >40.0 |
| 103 | 2.50 | 2.50 | 2.50 | 10.0 | 2.50 |
| 105 | 2.50 | 2.50 | 2.50 | >40.0 | >40.0 |
| 107 | 2.50 | 2.50 | 2.50 | 2.50 | 10.0 |
| 119 | 2.50 | 2.50 | 2.50 | 10.0 | >40.0 |
| 128 | 0.63 | 0.63 | 0.63 | >40.0 | 10.0 |
| 132 | 10.0 | 10.0 | 10.0 | 10.0 | 10.0 |
| 133 | 2.50 | 2.50 | 2.50 | 10.0 | 10.0 |
| 134 | 10.0 | 10.0 | 10.0 | 10.0 | 10.0 |
| 135 | 0.63 | 0.63 | 0.63 | 2.50 | >40.0 |
| 136 | 2.50 | 2.50 | 2.50 | 2.50 | 2.50 |
| 137 | 2.50 | 2.50 | 2.50 | 2.50 | 2.50 |
| 138 | 2.50 | 2.50 | 2.50 | 10.0 | >40.0 |
| 139 | 2.50 | 2.50 | 2.50 | 2.50 | 2.50 |

D. COMPOSITION EXAMPLES

"Active ingredient" (A.I.) as used throughout these examples relates to a compound of formula (I) a pharmaceutically acceptable addition salt, a stereochemically isomeric form thereof or a N-oxide form thereof.

EXAMPLE D.1

Oral Drops 500 grams of the A.I. was dissolved in 0.5 l of 2-hydroxypropanoic acid and 1.5 l of the polyethylene glycol at 60–80° C. After cooling to 30–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE D.2

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.3

Film-coated Tablets
Preparation of Tablet Core
A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.
Coating
To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE D.4

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

What is claimed is:
1. A compound of formula

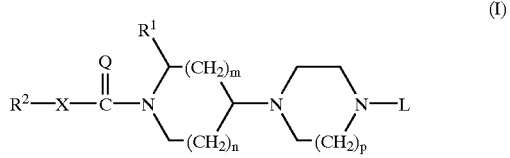

(I)

a N-oxide form, a pharmaceutically acceptable addition salt or a stereochemically isomeric form thereof, wherein
n is 1;
m is 1;
p is 1;

=Q is =O or =NR$^3$;

X is a covalent bond or a bivalent radical of formula —O—, —S—, —NR$^3$—;

R$^1$ is Ar$^1$, Ar$^1$C$_{1-6}$alkyl or di(Ar$^1$)C$_{1-6}$alkyl, wherein each C$_{1-6}$alkyl group is optionally substituted with hydroxy, C$_{1-4}$alkyloxy, oxo or a ketalized oxo substituent of formula —O—CH$_2$—H$_2$—O— or —O—CH$_2$—H$_2$—H$_2$—O—;

R$^2$ is Ar$^2$, Ar$^2$C$_{1-6}$alkyl, Het$^1$ or Het$^1$C$_{1-6}$alkyl;

R$^3$ is hydrogen or C$_{1-6}$alkyl;

L is Ar$^3$; C$_{1-6}$alkyl; C$_{1-6}$alkyl substituted with 1 or 2 substituents selected from hydroxy, C$_{1-6}$alkyloxy, Ar$^3$, Ar$^3$C$_{1-6}$alkyloxy and Het$^2$; C$_{3-6}$alkenyl; Ar$^3$C$_{3-6}$alkenyl; di(Ar$^3$)C$_{3-6}$alkenyl or a radical of formula

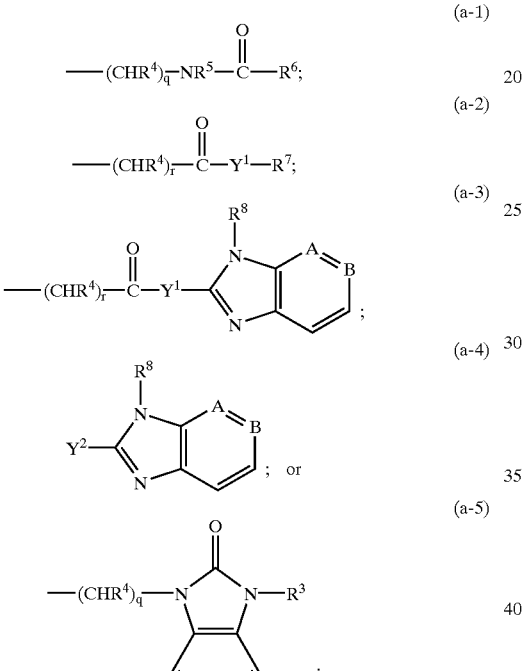

wherein each q independently is 2, 3 or 4;

each r is 0, 1, 2, 3 or 4;

each Y$^1$ independently is a covalent bond, —O— or NR$^3$;

Y$^2$ is a covalent bond, C$_{1-4}$alkanediyl or —C$_{1-4}$alkylNR$^3$—;

each —A=B— independently is a bivalent radical of formula —CH=CH—, —N=CH— or —CH=N—;

each R$^4$ independently is hydrogen, C$_{1-6}$alkyl, Ar$^2$ or Ar$^2$C$_{1-6}$alkyl;

R$^5$ is hydrogen, C$_{1-6}$alkyl or Ar$^3$;

R$^6$ is C$_{1-6}$alkyl, Ar$^3$, Ar$^3$C$_{1-6}$alkyl, di(Ar$^3$)C$_{1-6}$alkyl, Ar$^3$C$_{3-7}$cycloalkyl, or indolyl;

R$^7$ is Ar$^3$; Ar$^3$C$_{1-6}$alkyl; di(Ar$^3$)C$_{1-6}$alkyl; C$_{1-6}$alkyl; C$_{3-7}$cycloalkyl; C$_{3-7}$cycloalkyl substituted with Ar$^3$; oxazolyl; oxazolyl substituted with halo or C$_{1-6}$alkyl; thiazolyl; thiazolyl substituted with halo or C$_{1-6}$alkyl; imidazolyl; imidazolyl substituted with Ar$^3$, C$_{1-6}$alkyl, Ar$^3$C$_{1-6}$alkyl or halo; indolinyl; indolinyl substituted with C$_{1-4}$alkyl; 2,3,4-trihydroquinolinyl; pyrrolidinyl or furanyl;

each R$^8$ independently is hydrogen, C$_{1-6}$alkyl, C$_{3-7}$cycloalkyl or a radical of formula —Alk—R$^{11}$ (b-1) or —Alk—Z—R$^{12}$ (b-2);

wherein Alk is C$_{1-6}$alkanediyl;

Z is a bivalent radical of formula —O—, —S— or —NR$^3$—;

R$^{11}$ is phenyl; phenyl substituted with 1 or 2 substituents selected from halo, C$_{1-6}$alkyl or C$_{1-6}$alkyloxy; furanyl; furanyl substituted with 1 or 2 substituents selected from C$_{1-6}$alkyl or hydroxyC$_{1-6}$alkyl; thienyl; thienyl substituted with 1 or 2 substituents selected from halo or C$_{1-6}$alkyl; oxazolyl; oxazolyl substituted with 1 or 2 C$_{1-6}$alkyl substituents; thiazolyl; thiazolyl substituted with 1 or 2 C$_{1-6}$alkyl substituents; pyridinyl or pyridinyl substituted with 1 or 2 C$_{1-6}$alkyl substituents;

R$^{12}$ is C$_{1-6}$alkyl or C$_{1-6}$alkyl substituted with hydroxy, carboxyl or C$_{1-6}$alkyloxycarbonyl;

Ar$^1$ is phenyl; phenyl substituted with 1, 2 or 3 substituents each independently selected from halo, C$_{1-4}$alkyl, haloC$_{1-4}$alkyl, cyano, aminocarbonyl, C$_{1-4}$alkyloxy or haloC$_{1-4}$alkyloxy;

Ar$^2$ is naphtalenyl; phenyl; phenyl substituted with 1, 2 or 3 substituents each independently selected from hydroxy, halo, cyano, nitro, amino, mono- or di(C$_{1-4}$alkyl)amino, C$_{1-4}$alkyl, haloC$_{1-4}$alkyl, C$_{1-4}$alkyloxy, haloC$_{1-4}$alkyloxy, carboxyl, C$_{1-4}$alkyloxycarbonyl, aminocarbonyl and mono- or di(C$_{1-4}$alkyl) aminocarbonyl;

Ar$^3$ is phenyl or phenyl substituted with 1, 2 or 3 substituents selected from halo, hydroxy, amino, nitro, aminocarbonyl, C$_{1-6}$alkyl, haloC$_{1-6}$alkyl or C$_{1-6}$alkyloxy;

Het$^1$ is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, C$_{1-4}$alkyl or mono-, di- or tri(halo)methyl; and Het$^2$ is a heterocycle selected from 1,4-dihydro-5-oxotetrazol-1-yl, imidazo[1,2-a]pyridinyl, oxazolyl or imidazolyl; each of said heterocycles may be substituted with 1 or where possible 2 substituents selected from C$_{1-4}$alkyl and Ar$^3$.

2. A compound according to claim 1 wherein L is C$_{1-6}$alkyl; C$_{1-6}$alkyl substituted with hydroxy; C$_{3-6}$alkenyl; Ar$^3$; Ar$^3$C$_{1-6}$alkyl; di(Ar$^3$)C$_{1-6}$alkyl; Ar$^3$C$_{3-6}$alkenyl; di(Ar$^3$)C$_{1-6}$alkenyl; or a radical of formula (a-1), (a-2), (a-4) or (a-5) wherein R$^7$ is Ar$^3$; Ar$^3$C$_{1-6}$alkyl; di(Ar$^3$)C$_{1-6}$alkyl; C$_{1-6}$alkyl; C$_{3-7}$cycloalkyl; C$_{3-7}$cycloalkyl substituted with Ar$^3$; oxazolyl; oxazolyl substituted with halo or C$_{1-6}$alkyl; thiazolyl; thiazolyl substituted with halo or C$_{1-6}$alkyl; imidazolyl; imidazolyl substituted with Ar$^3$, C$_{1-6}$alkyl, Ar$^3$C$_{1-6}$alkyl or halo; pyrrolidinyl or furanyl;

Ar$^3$ is is phenyl or phenyl substituted with 1, 2 or 3 substituents selected from halo, hydroxy, amino, aminocarbonyl, C$_{1-6}$alkyl, haloC$_{1-6}$alkyl or C$_{1-6}$alkyloxy;

Het$^1$ is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl or mono-, di- or tri(halo)methyl.

3. A compound as claimed in claim 2 wherein $R^1$ is $Ar^1C_{1-6}$alkyl, $R^2$ is phenyl substituted with 2 substituents selected from methyl and trifluoromethyl, X is a covalent bond and =Q is =O.

4. A compound as claimed in claim 3 wherein $R^1$ is phenylmethyl; $R^2$ is phenyl substituted with 2 substituents selected from methyl or trifluoromethyl; X is a covalent bond; and =Q is =O.

5. A compound as claimed in claim 3 wherein L is a radical of formula (a-2) wherein $R^4$ is hydrogen or phenyl; r is 0 or 1; $Y^1$ is a covalent bond, —O— or —NH—; $R^7$ is pyrrolidinyl; furanyl; 1-phenylcyclohexanyl; diphenylmethyl; or phenyl substituted with 1, 2 or 3 substituents each independently selected from methyl, methoxy or chloro.

6. A compound as claimed in claim 5 wherein the compound has the trans configuration.

7. A compound as claimed in claim 5 wherein the compound has the cis configuration.

8. A composition comprising a pharmaceutically acceptable carrier, and as active ingredient therapeutically effective amount of a compound as claimed in claim 1.

9. A process of preparing a composition as claimed in claim 8, characterized in that the pharmaceutically acceptable carrier is intimately mixed with a therapeutically effective amount of the compound.

10. A method of treating a warm-blooded animal suffering from a disease selected from the group consisting of pain, asthma and emesis comprising administering to the warm-blooded animal a therapeutically effective amount of a compound of claim 1.

* * * * *

UNITED STATES PATENT AND TRADEMARK OFFICE
CERTIFICATE OF CORRECTION

PATENT NO.    : 6,521,621 B1
DATED         : February 18, 2003
INVENTOR(S)   : Frans Eduard Janssens et al.

It is certified that error appears in the above-identified patent and that said Letters Patent is hereby corrected as shown below:

<u>Column 75,</u>
Line 7, replace "–O-$CH_2$-$H_2$-O-or-O-$CH_2$-$H_2$-$H_2$-O-" with -- -O-$CH_2$-$CH_2$-O-or-$CH_2$-$CH_2$-$CH_2$-O- --

<u>Column 76,</u>
Line 64, replace "$Ar^3$ is is phenyl" with -- $Ar^3$ is phenyl --

Signed and Sealed this

Eighteenth Day of May, 2004

JON W. DUDAS
*Acting Director of the United States Patent and Trademark Office*